(12) United States Patent
Chambers et al.

(10) Patent No.: US 7,739,971 B2
(45) Date of Patent: Jun. 22, 2010

(54) SYSTEMS AND METHODS FOR ASSEMBLING COMPONENTS OF A FABRIC-COVERED PROSTHETIC HEART VALVE

(75) Inventors: Freeman G. Chambers, Irvine, CA (US); Lawrence J. Zysman, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 1385 days.

(21) Appl. No.: 11/147,797

(22) Filed: Jun. 7, 2005

(65) Prior Publication Data
US 2006/0276889 A1 Dec. 7, 2006

(51) Int. Cl.
*D05B 35/00* (2006.01)
*A61F 2/24* (2006.01)

(52) U.S. Cl. .......................... 112/475.01; 112/475.14; 112/475.17; 623/2.1

(58) Field of Classification Search .................. 112/153, 112/63, 308, 475.01, 475.08; 623/2.1–2.19, 623/2.38–2.41
See application file for complete search history.

(56) References Cited

U.S. PATENT DOCUMENTS

| 3,709,175 | A | * | 1/1973 | Edwards et al. ........ 112/470.14 |
| 3,710,744 | A | | 1/1973 | Goodenough et al. |
| 4,035,849 | A | | 7/1977 | Angell et al. |
| 4,388,735 | A | | 6/1983 | Ionexcu et al. |
| 4,626,255 | A | | 12/1986 | Reichart et al. |
| 4,680,031 | A | * | 7/1987 | Alonso ...................... 623/2.13 |
| 5,488,789 | A | * | 2/1996 | Religa et al. ............... 38/102.2 |
| 5,895,420 | A | | 4/1999 | Mirsch, II et al. |
| 5,928,281 | A | | 7/1999 | Huynh et al. |
| 6,295,940 | B1 | | 10/2001 | Shonteff |
| 6,338,740 | B1 | | 1/2002 | Carpentier |
| 6,558,418 | B2 | | 5/2003 | Carpentier et al. |
| 6,736,845 | B2 | | 5/2004 | Marquez et al. |
| 6,755,141 | B2 | | 6/2004 | Musco et al. |

(Continued)

FOREIGN PATENT DOCUMENTS

WO    WO96/40012    12/1996

OTHER PUBLICATIONS

Edwards Heart Valve Assembly Instructions, 5 pages, dated Dec. 19, 2002 (Trade Secret, submitted under seal).

*Primary Examiner*—Ismael Izaguirre
(74) *Attorney, Agent, or Firm*—Rajiv Yadav, Esq.; Guy Cumberbatch, Esq.

(57) ABSTRACT

A system and method for assembling a prosthetic heart valve, including a procedure for tightly wrapping fabric around a heart valve support stent having a highly contoured undulating outflow edge. A mandrel retains tension without manual assistance in a tubular length of fabric wrapped over the support stent, and includes relatively axially movable inner and outer clamping mechanisms and a pedestal tube on which the support stent rests. The clamping mechanisms include clamps that pull the fabric only in the support stent cusps. The mandrel assembly may be placed in a chuck of a sewing machine system for automatically forming the seam. A small shuttle with bobbin thread reciprocates within a channel inside of the support stent and cooperates with the sewing machine needle to form a lock-stitch in the fabric tube. The mechanization of the fabric covering procedure greatly enhances manufacturing throughput and reduces ergonomic strain on workers.

24 Claims, 17 Drawing Sheets

U.S. PATENT DOCUMENTS 7,073,456 B2 * 7/2006 Phillips et al. ......... 112/475.17
7,185,597 B1 * 3/2007 Phillips et al. ......... 112/475.04
2004/0148018 A1 7/2004 Carpentier et al.
2004/0176839 A1 9/2004 Huynh et al.

* cited by examiner

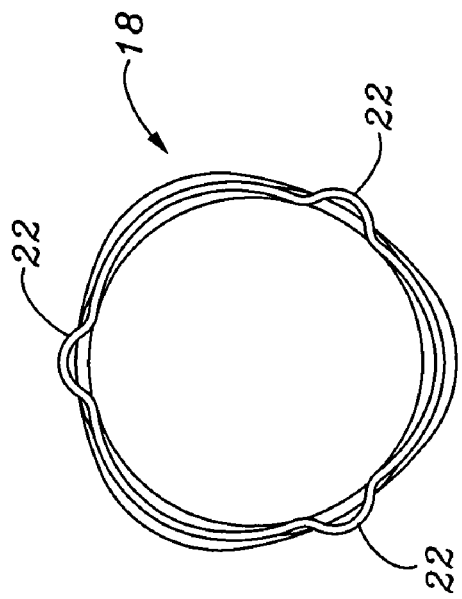
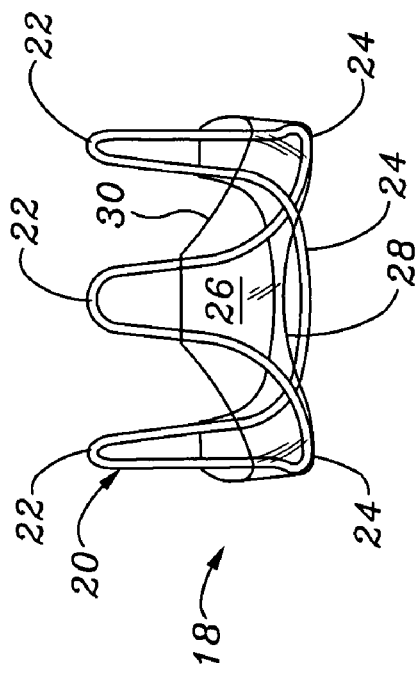
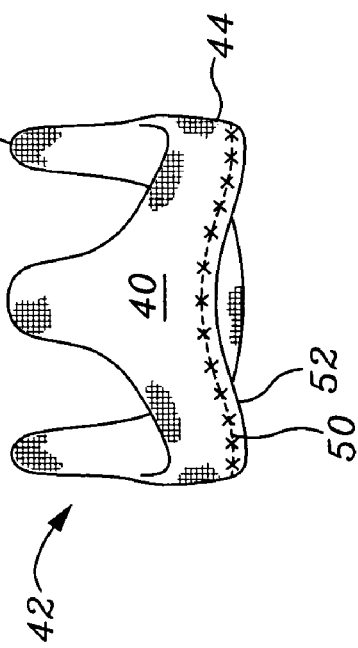

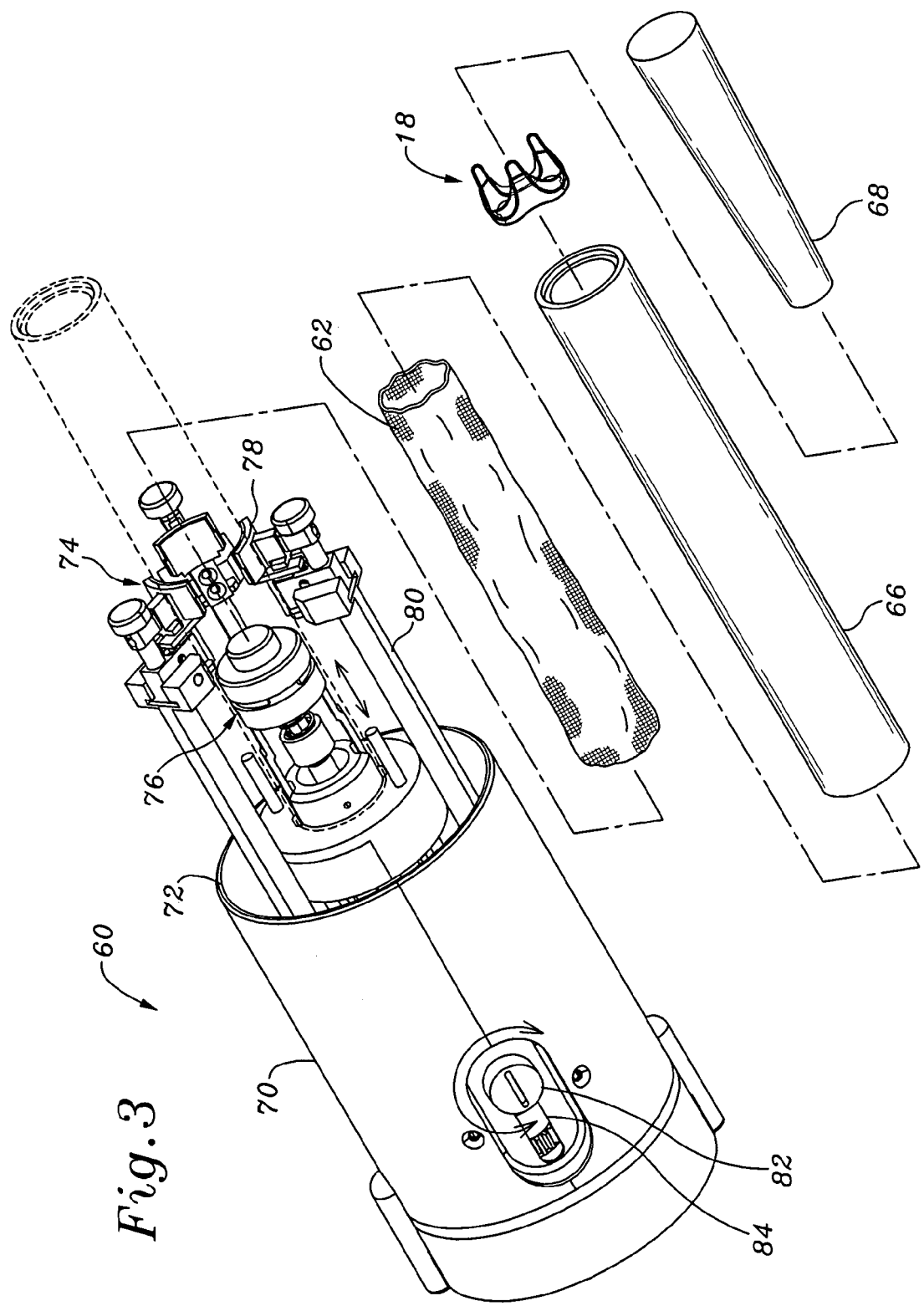

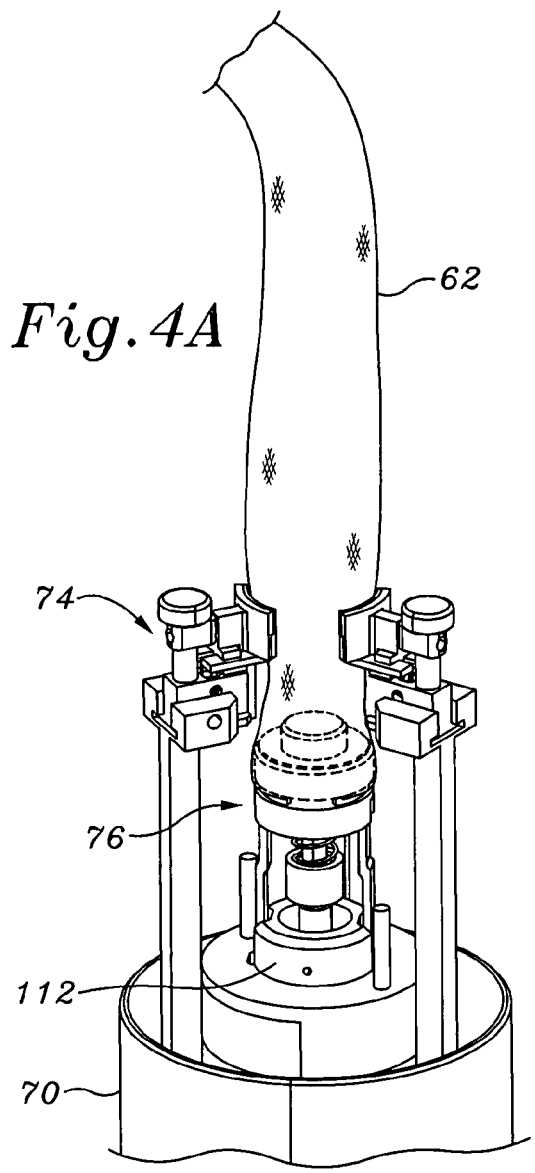
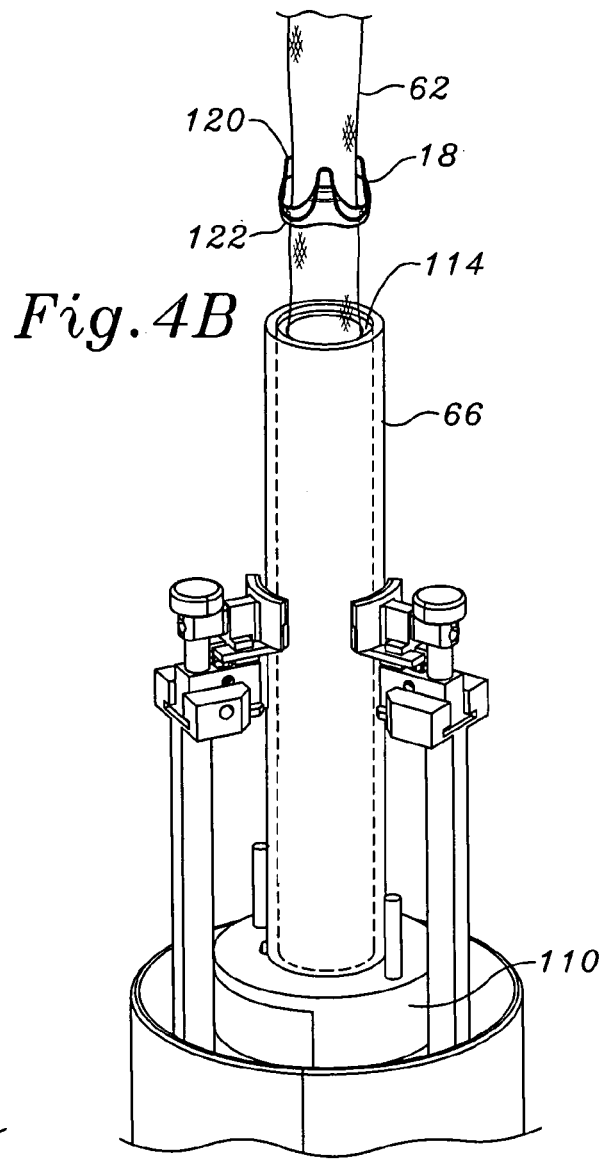
*Fig. 4A* *Fig. 4B*
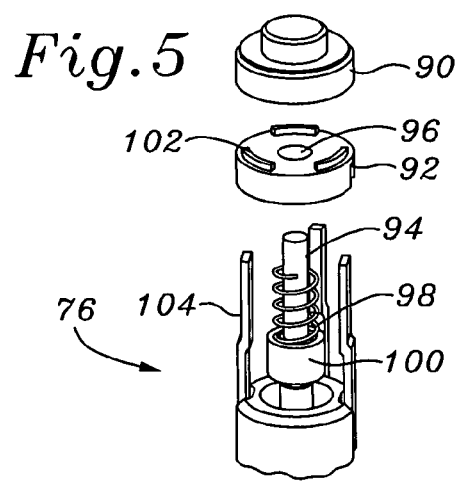
*Fig. 5*

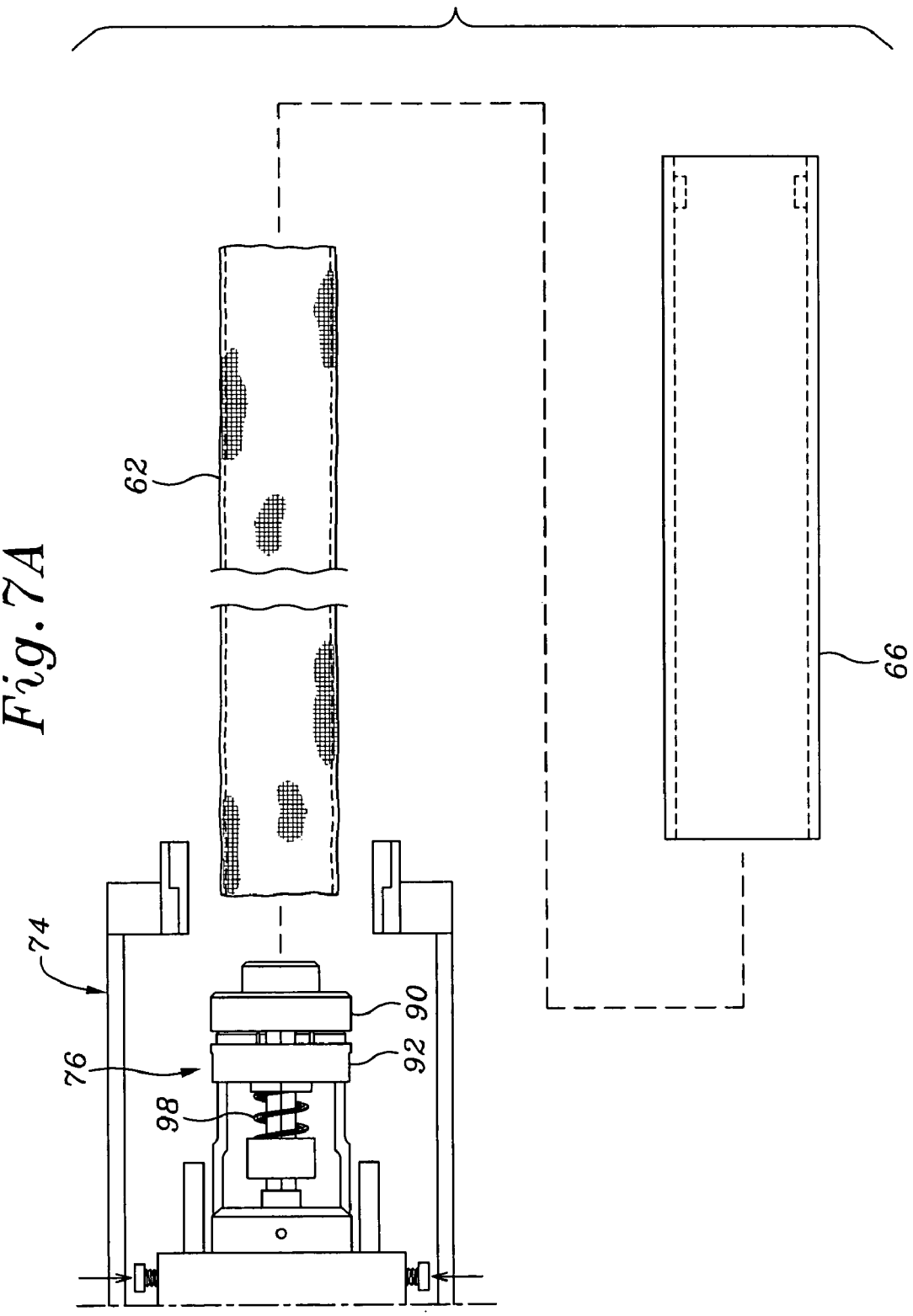

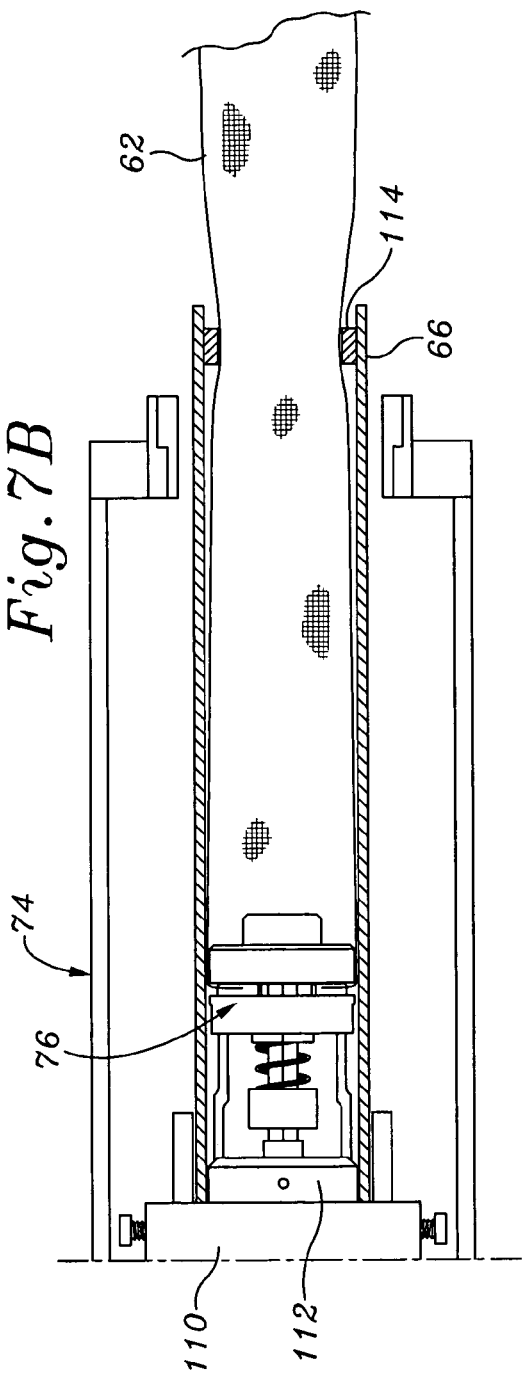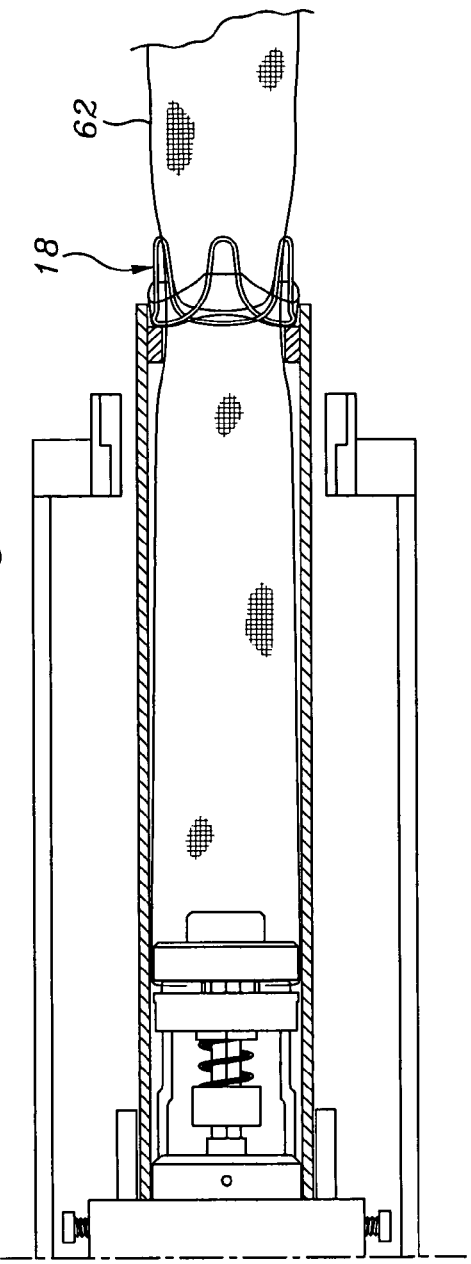

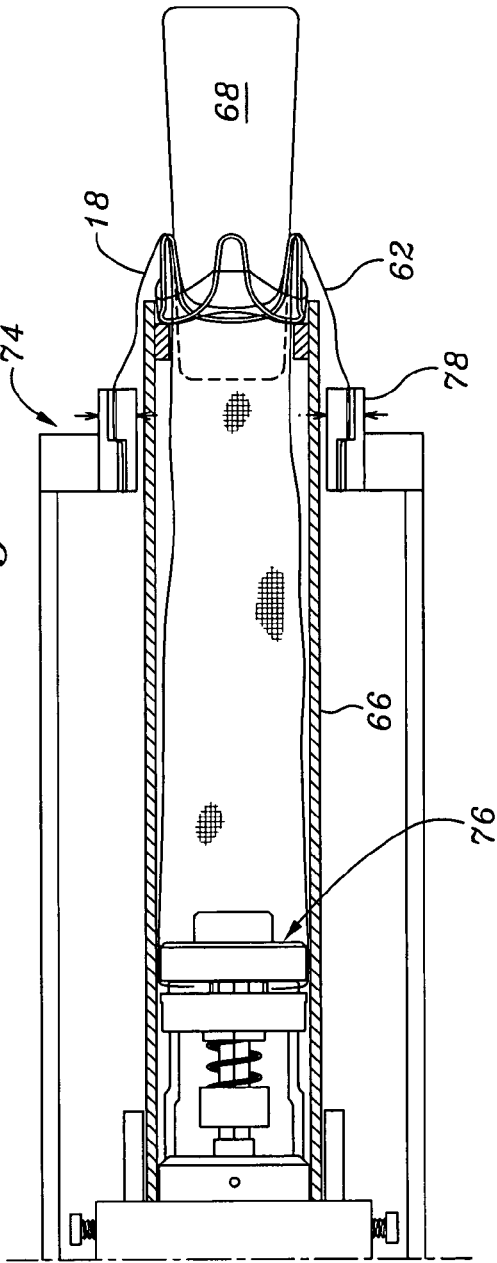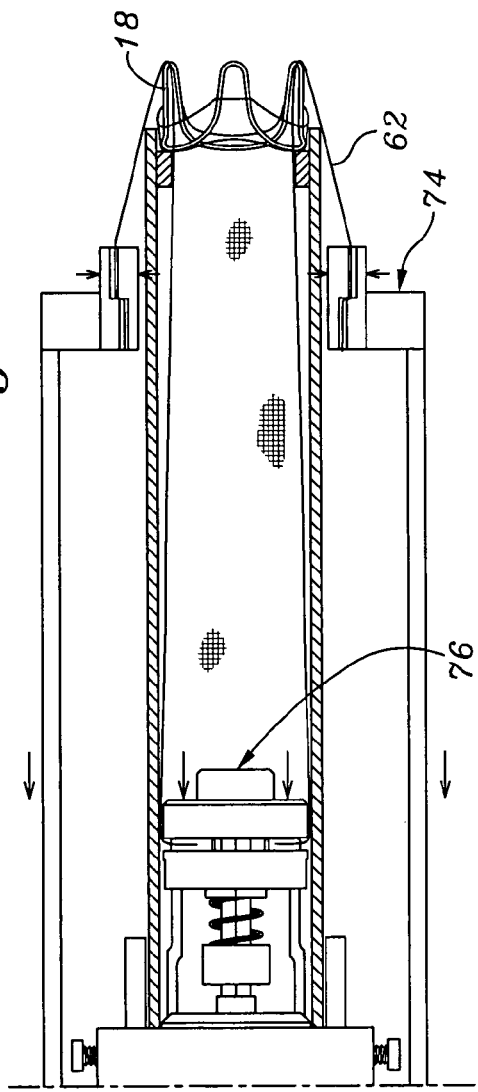

SYSTEMS AND METHODS FOR ASSEMBLING COMPONENTS OF A FABRIC-COVERED PROSTHETIC HEART VALVE

FIELD OF THE INVENTION

The present invention relates generally to medical devices, and more particularly to a system that facilitates the assembly of components of a fabric-covered prosthetic heart valve, and associated methodology.

BACKGROUND OF THE INVENTION

One of the primary classes of artificial heart valves or prostheses is a "tissue-type" or "bioprosthetic" valve having flexible leaflets that function much like those of a natural human heart valve and imitate their natural action to coapt against each other and ensure one-way blood flow. In tissue valves, a whole xenograft valve (e.g., porcine) or a plurality of xenograft leaflets (e.g., bovine pericardium) typically provide fluid occluding surfaces. Synthetic leaflets have been proposed, and thus the term "flexible leaflet valve" refers to both natural and artificial "tissue-type" valves. Two or more flexible leaflets are mounted within a peripheral stent structure that usually includes posts or commissures extending in the outflow direction to mimic natural fibrous commissures in the native aortic annulus (the same construction may be used for the mitral annulus, though it does not correspond as closely with the mitral anatomy).

In most flexible leaflet valves, metallic or polymeric structure provides base support for the flexible leaflets, which extend therefrom. One such support is an elastic "support frame," sometimes called a "wireform," which has a plurality (typically three) of large radius cusps supporting the inflow cusp region of the leaflets of the bioprosthetic tissue (i.e., either a whole valve or three separate leaflets). The free ends of each two adjacent cusps converge somewhat asymptotically to form upstanding commissures that terminate in tips, each being curved in the opposite direction as the cusps, and having a relatively smaller radius. The wireform typically describes a conical tube with the commissure tips at the small diameter end. This provides an undulating reference shape to which a fixed edge of each leaflet attaches (via components such as fabric and sutures) much like the natural fibrous skeleton in the aortic annulus. Some valves include polymeric wireforms rather than metallic, for ease of manufacture or other reasons. For example, U.S. Pat. No. 5,895,420 discloses a plastic wireform that degrades in the body over time. In a hybrid construction, the CARPENTIER-EDWARDS Porcine Heart Valve and PERIMOUNT Pericardial Heart Valve available from Edwards Lifesciences of Irvine, Calif. both have ELGILOY wireforms surrounded by polymer bands.

U.S. Pat. No. 4,035,849 to Angell, et al., U.S. Pat. No. 4,388,735 to Ionescu, et al., and U.S. Pat. No. 4,626,255 to Reichart, et al. disclose various flexible leaflet prosthetic heart valves with fabric-covered stents. Another example of the construction of a flexible leaflet valve is seen in U.S. Pat. No. 5,928,281 to Huynh, et al., in which the exploded view of FIG. 1 illustrates a support stent comprising a fabric-covered wireform and a fabric-covered stent on either side of a leaflet subassembly. FIGS. 1A and 1B are elevational and top plan views, respectively, of an exemplary support stent 18 for a prosthetic heart valve similar to that disclosed in the patent to Huynh, et al. The support stent includes multiple cusps curved toward an axial inflow end alternating with multiple commissures projecting toward an axial outflow end, the support stent 18 defining an undulating outflow edge. The illustrated support stent 18 comprises a wireform 20 having three upstanding commissures 22 alternating with three cusps 24 of larger radii which generally circumscribe a tube. A circular supporting band 26 closely surrounds the wireform 20 and defines an inflow edge 28 and an outflow edge 30. The inflow edge of the band 26 conforms to the cusps 24 of the wireform 20, and may be curved in the outflow direction in between in the region of the wireform commissures 22. The outflow edge 30 extends approximately halfway up the wireform commissures 22, and dips down therebetween in the inflow direction. This type of support stent 18 forms the structural "spine" of a one-way prosthetic heart valve which may be implanted in any of the four orifices in the heart, though most commonly in either the mitral or aortic positions.

Components of the valve are usually assembled with one or more biocompatible fabric (e.g., Dacron, polyethylene terepthalate) coverings, and a fabric-covered sewing ring is provided on the inflow end of the stent. The fabric coverings provide anchoring surfaces for sutures to hold the flexible leaflets and sewing ring to the peripheral stent structure. In one of the assembly procedures, a tubular fabric is tightly wrapped around the undulating stent and sewn closed with one or more peripheral seams. Because of the undulating shape of the support stent, the process involves manually holding a tube of fabric around the stent and the sewing is typically accomplished in two stages; first, intermittent stitches are placed to secure the fabric in its gross position around the stent, and then a closely-spaced line of stitches is applied to complete the seam. The odd shape of the stent and the presence of two or more components being enclosed by the fabric cover necessitates that the holding and stitching operation is done manually, which makes it quite labor-intensive and time-consuming. Quality control in the manufacture of heart valves further increases the difficulty of the task because the fabric must be tightly fitted around the stent. This manual sewing procedure represents a substantial portion of the cost of the entire valve fabrication process. Furthermore, repetitive stress injuries can occur which is painful to the worker and indirectly increases the cost of making the valve. Indeed, most of the steps in assembling prosthetic heart valves are specialized, manual tasks performed in a clean room. Typically the components are held by the worker and sewn together at the same time, which is a laborious process considering the exacting nature of the quality control applied to the subsequent finished product.

There is thus a need for an improved method for assembling flexible heart valves that reduces the assembly time and reduces the instances of injury to the assembly-line workers.

SUMMARY OF THE INVENTION

The present invention provides an improved system for automatically sewing one of the stitches used in the construction of a prosthetic heart valve. In particular, the system includes a stent cloth stretching fixture for presenting heart valve components in a fixed and repeatable manner through a series of mechanisms that position, stretch, and hold the components in relative positions. The system of the present invention significantly improves speed and quality over current manual manufacturing practices. Further, the system eliminates a significant source of ergonomic stress and injury.

In accordance with one aspect of the present invention, a system for assembling components of a flexible leaflet prosthetic heart valve having a generally tubular fabric-covered leaflet support stent defining a central axis is provided. The system comprises a mandrel for retaining tension without manual assistance in a tubular length of fabric wrapped over an outflow end of a heart valve support stent, wherein the outflow end includes an undulating contour and the mandrel is adapted to retain tension in the tubular length of fabric so that it conforms to the undulating contour. The system also includes a means for forming a seam in the tubular length of fabric to enclose the stent.

The undulating contour of the outflow end may include multiple cusps curved toward an axial inflow end alternating with multiple commissures projecting toward an axial outflow end, and the mandrel includes separate clamps for the fabric corresponding to the stent cusps. There are desirably three inflow cusps and three outflow commissures alternating around a periphery of the support stent, wherein the mandrel clamps the fabric beyond an axial inflow end of the stent in peripheral locations corresponding to the cusps. Accordingly the mandrel may include an outer clamping mechanism comprising three clamp members oriented 120° apart in each of which is adapted to clamp a section of fabric, and an inner clamping mechanism comprising two disks between which one end of the tubular length of fabric may be clamped. The mandrel further may include a pedestal tube that fits on the mandrel and holds the support stent, the pedestal tube, outer clamping mechanism, and inner clamping mechanism all being relatively axially movable. In a preferred embodiment, the means for forming a seam comprises an electric sewing machine.

Another aspect of the invention is a system for assembling a prosthetic heart valve, two components of a prosthetic heart valve, a mandrel having at least one clamp for holding and maintaining in a precise positional relationship the two heart valve components, and an electric sewing machine including a needle for forming a seam in fabric to join the two components.

The two components desirably comprise a fabric covering and a generally tubular prosthetic heart valve support stent having multiple cusps curved toward an axial inflow end alternating with multiple commissures projecting toward an axial outflow end. The mandrel may be disposed beyond the inflow end of the support stent and having at least one clamp for holding and maintaining in a taut fashion the fabric covering over the outflow end of the support stent. The electric sewing machine desirably further including a shaft for rotating the commissure clamps, and wherein the needle is positioned to form a seam in the fabric covering at the inflow end of the support stent. Multiple commissure clamps hold the fabric-covered support stent commissures, and the sewing machine may include a chuck for receiving and rotating the mandrel about the stent axis. In one embodiment, the sewing machine is adapted to axially displace the support stent as it rotates, and the chuck is adapted to simultaneously rotate and axially displace the mandrel.

A method of assembling a prosthetic heart valve is also provided by the present invention. The method includes the steps of:
  providing a generally tubular support stent that includes multiple cusps curved toward an axial inflow end alternating with multiple commissures projecting toward an axial outflow end, the support stent having an undulating outflow edge;
  wrapping a tubular length of fabric over the support stent;
  providing a support stent holding mandrel;
  retaining tension using the mandrel in the tubular length of fabric such that the fabric is held tautly along the undulating outflow edge; and
  forming a seam in the tubular length of fabric adjacent the inflow edge of the support stent.

The mandrel further includes an inner clamping mechanism, an outer clamping mechanism, and a pedestal tube, and wherein the method further may include the steps of:
  securing one end of the tubular length of fabric with the inner clamping mechanism;
  passing the free end of the tubular length of fabric through the pedestal tube and through the support stent;
  positioning the support stent on the pedestal tube;
  inverting the second end of the tubular length of fabric and wrapping it around the support stent; and
  securing the second end of the tubular length of fabric with the outer clamping mechanism.

The method may further include tightening the tubular length of fabric around the support stent by relatively axially displacing the inner and outer clamping mechanisms with respect to the pedestal tube. Desirably, the inner and outer clamping mechanisms each include discrete clamps spaced apart 120° from each other that directly tension the fabric only at the cusps of the support stent. The fabric-wrapped commissures of the support stent are preferably held with a plurality of commissure clamps and the pedestal tube is separated from the support stent by relatively axially displacing the pedestal tube with respect to the commissure clamps.

The mandrel further may include an inner clamping mechanism, an outer clamping mechanism, and a pedestal tube, and wherein the method further includes:
  positioning the support stent on the pedestal tube;
  securing opposite ends of the tubular length of fabric with the inner and outer clamping mechanisms, respectively; and
  tensioning the tubular length of fabric around the support stent by relative movement of both the inner and outer clamping mechanisms with respect to the pedestal tube.

Preferably, the mandrel is positioned within a sewing machine system adapted to rotate the mandrel about an axis, the sewing machine system further including a spindle on which are mounted a plurality of commissure clamps. The method therefore includes holding the fabric-wrapped commissures of the support stent with the commissure clamps and separating the pedestal tube from the support stent by relatively axially displacing the pedestal tube with respect to the commissure clamps. In some cases, the support stent has an undulating inflow edge, and the spindle and the mandrel are simultaneously axially displaced and rotated while forming a seam with a needle passing through the length of tubular fabric adjacent the inflow edge. The undulating inflow edge may be mapped prior to forming a seam, and movement of the spindle and mandrel may be controlled based on the mapped inflow edge.

A further aspect of the invention is a sewing machine system for forming a tubular seam in a tubular fabric piece around a medical device. The sewing machine system includes a clamp assembly for holding and rotating the tubular fabric piece wrapped around the medical device. A reciprocating needle carries a needle thread mounted for linear motion through the tubular fabric piece held by the clamp assembly. A shuttle carrying a bobbin thread is arranged to reciprocate in a linear direction perpendicular to the direction of motion of the needle and on the inside of the tubular fabric piece. A channel within which the shuttle slides passes through the tubular fabric piece, and a driving mechanism loosely couples to the shuttle and moves it back-and-forth within the channel past the needle. A driving mechanism includes a pivoting finger having a shoulder for pushing on a proximal end of the shuttle and a spherical bump that fits within a spherical depression formed in the shuttle. Preferably, the shuttle has a diametric dimension of about 8 millimeters or less.

In one embodiment, the shuttle has a pointed distal end and is arranged to pass through a loop of the needle thread to form a lock-stitch. Desirably, the shuttle comprises a housing within which is mounted a shaft that carries a coil of the bobbin thread, the shuttle further including a solid member for tensioning the bobbin thread before it pays off of the coil, the solid member being made of a material that will not deteriorate and thus contaminate a clean room environment. The pivoting finger pivots outward from an open side of the channel to expose the shuttle and facilitate exchange of bobbin threads.

In a further embodiment, the present invention provides a sewing machine system for forming a tubular seam in a tubular fabric piece around a medical device including a clamp assembly for holding and rotating the tubular fabric piece wrapped around the medical device. A reciprocating needle carries a needle thread mounted for linear motion through the tubular fabric piece held by the clamp assembly. A shuttle carries a coil of bobbin thread and reciprocates in a linear direction perpendicular to the direction of motion of the needle and on the inside of the tubular fabric piece. The shuttle has a diametric dimension of about 8 millimeters or less and carries a solid member for tensioning the bobbin thread before it pays off of the coil, the solid member being made of a material that will not deteriorate and thus contaminate a clean room environment.

The system preferably includes a channel passing through the tubular fabric piece and within which the shuttle slides, and a driving mechanism that loosely couples to the shuttle and moves it back-and-forth within the channel past the needle. The driving mechanism includes a pivoting finger having a shoulder for pushing on a proximal end of the shuttle and a spherical bump that fits within a spherical depression formed in the shuttle. Desirably, the shuttle has a pointed distal end and is arranged to pass through a loop of the needle thread to form a lock-stitch. The shuttle comprises a housing having a recess on its exterior across which a length of the bobbin thread passes. The solid member desirably comprises one of a pair of members mounted on a second shaft in the housing and biased toward one another, and between which the bobbin thread passes to impart tension thereto. The solid members may be made of acetal (Delrin), polytetrafluoroethylene (Teflon), or a suitable metal.

The present invention further provides a sewing machine system for forming a tubular seam in a tubular fabric piece. The sewing machine system includes a clamp assembly for holding and rotating the tubular fabric piece. A reciprocating needle carrying a needle thread mounts for linear motion through the tubular fabric piece held by the clamp assembly. A shuttle carrying a bobbin thread is arranged to reciprocate in a linear direction perpendicular to the direction of motion of the needle and on the inside of the tubular fabric piece, the shuttle having a diametric dimension of 8 mm or less. Desirably, the shuttle has a pointed distal end and is arranged to pass through a loop of a length of thread carried by the needle to form a lock-stitch. The system further may include a stationary channel passing through the tubular fabric piece and within which the shuttle slides, and a driving mechanism that loosely couples to the shuttle and moves it back-and-forth within the channel. Preferably, the driving mechanism includes a pivoting finger having a shoulder for pushing on a proximal end of the shuttle and a spherical bump that fits within a spherical depression formed in the shuttle. In one embodiment, the shuttle comprises a housing within which is mounted a bobbin shaft that carries a coil of the bobbin thread. At the same time the shuttle also includes a second shaft having a pair of members biased toward one another and between which the bobbin thread passes to impart tension thereto. The system further may include a mechanism for rotating and axially displacing the clamp assembly.

In accordance with a still further aspect, the present invention provides a method of assembling a prosthetic heart valve, including providing a generally tubular heart valve support stent that includes a first edge and an axially-opposite second edge. A tubular length of fabric is wrapped over the first edge of the support stent such that two free ends of the tubular length of fabric continue past the second edge. Tension is retained in the tubular length of fabric such that the fabric is held tautly along the first edge. The peripheral contour of the second edge of the support stent is mapped with an imaging system, and then a seam is formed in the tubular length of fabric closely adjacent the second edge of the support stent using an automated sewing system having a needle whose position relative to the second edge is responsive to the mapped contour of the second edge. Desirably, the second edge of the support stent is an inflow edge that has an undulating contour, the method further including simultaneously axially displacing the support stent while forming the seam with the needle of the automated sewing system. The first edge of the support stent is an outflow edge that includes multiple cusps curved toward an axial inflow end alternating with multiple commissures projecting toward an axial outflow end, and tension is retained in the fabric without manual assistance so that the fabric conforms to the cusps and commissures of the outflow edge. Desirably, the seam is formed within about 0.030 inches (0.762 mm) of the inflow edge. In one embodiment, the imaging system comprises an ultraviolet light and a camera A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

FIGS. 1A and 1B are elevational and top plan views, respectively, of an exemplary support stent used in the construction of a prosthetic heart valve;

FIG. 2 is an elevational view of the support stent of FIGS. 1A and 1B after having being tightly covered with fabric in accordance with an assembly procedure of the present invention;

FIG. 3 is an exploded perspective view of a mandrel and associated assembly components used in an exemplary fabric covering procedure of the present invention;

FIGS. 4A and 4B are perspective views of the mandrel of FIG. 3 in two initial stages of the fabric covering procedure;

FIG. 5 is an exploded perspective view of a disk assembly that captures one end of a tubular portion of fabric used to cover a support stent;

FIGS. 7A-7G are elevational views of the mandrel of FIG. 3 and associated assembly components illustrating several sequential steps of the fabric covering procedure;

DESCRIPTION OF THE PREFERRED EMBODIMENTS

Figure 6:
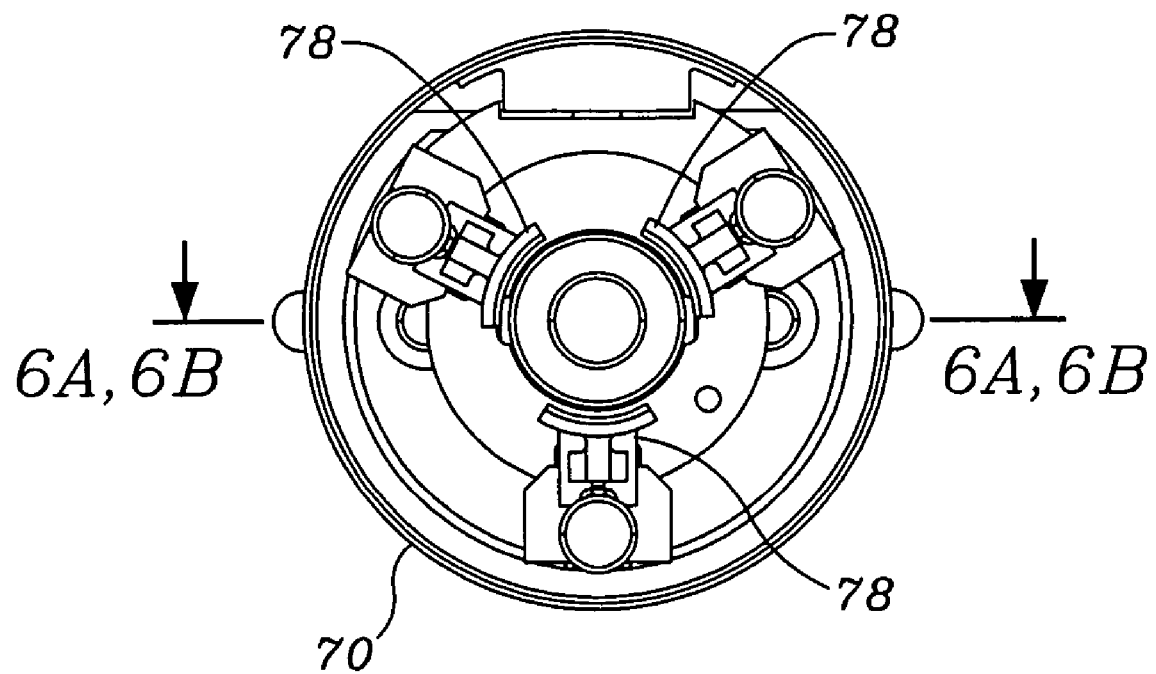
FIG. 6 is a top plan view of the mandrel of FIG. 3.

The present invention provides a system for automating one or more steps of a prosthetic heart valve fabrication procedure. The steps of the procedure illustrated and described involve stretching and sewing a tubular piece of fabric around a support stent. It should be understood by those of skill in the art that the illustrated support stent is only exemplary, and the present invention can be used to cover various support stents. Furthermore, various aspects of the present invention may be used in other steps of a heart valve fabrication process. For example, mechanisms similar to those shown and described may be used to cover other parts of a prosthetic heart valve with fabric. Up to now, prosthetic heart valve assembly has been an almost entirely manual, labor-intensive process. The present invention therefore represents a pioneering effort to automate at least some of the process of assembling heart valves.

The present invention involves generally two stages: a first stage of stretching a portion of fabric around a support stent, and a second stage of fastening or sewing the fabric. Either or both of the stages may be mechanized, with the other being performed manually. Desirably, at least the first stage of stretching a portion of fabric around a support stent is mechanized such that the subsequent sewing step may be performed with a means for forming a seam in the fabric, such as with a sewing machine needle or by hand using a needle. In the context of the present invention, the term "mechanized" means that some or all of a particular step in the procedure is accomplished using mechanical means or tools. "Mechanized" does not necessarily mean "automated," in that manual operation of the various mechanical means may be required. Ultimately, one or more steps in the procedure may be automated, or self-driven, with the mechanized portions described herein incorporated into the entire process as subcomponents. However, because of the relatively small numbers of heart valves manufactured, and the attendant care taken in the overall process, the mechanized assembly enhancements described herein may so greatly improve the efficiency and reliability of the process that complete automation will not be required.

With reference now to FIG. 2, the exemplary support stent of FIGS. 1A-1B is shown covered with fabric 40. The fabric-covered support stent 42 is generally tubular and includes multiple cusps 44 curved toward an axial inflow end alternating with multiple commissures 46 projecting toward an axial outflow end. The support stent 42 describes an undulating outflow edge 48 about which the fabric 40 is tautly held. A seam 50 adjacent a serpentine or undulating inflow edge 52 secures the fabric 40 about the support stent. The seam 50 is shown slightly axially above the inflow edge 52 for clarity, although it may be located directly at the inflow edge or even inside the support stent. The system of the present invention maintains the fabric 40 about the inner support stent in a taut manner while the seam 50 is formed just beyond the inflow edge 52. It should be understood that after the seam 50 is formed, tension in the fabric may cause the seam 50 to migrate, thus leading to its slightly variable final location.

FIG. 3 illustrates a mandrel 60 for retaining tension without manual assistance in a tubular length of fabric 62 wrapped over a leaflet support stent 18. As explained above, the leaflet support stent 18 may take a variety of forms but is illustrated in the configuration of FIG. 1. The mandrel 60 is shown exploded along with several associated system components for wrapping the fabric 62 over the stent 18. Specifically, the system further includes a pedestal tube 66 and a stabilizing cone 68. In the context of the present invention, the term "mandrel" means a mechanism used to secure or support an element being worked on, in particular a clamping mechanism for the leaflet support stent 18 during a process of covering it with fabric.

The mandrel 60 comprises a base having a generally cylindrical outer housing 70 defining a cavity therewithin. A fabric clamping mechanism extends through an open mouth 72 of the housing 70 and includes an outer clamping mechanism 74 and an inner clamping mechanism 76. The outer clamping mechanism 74 actually consists of a plurality (preferably three) of separate clamp members 78 supported on stanchions 80. The inner clamping mechanism 76 is shown in more detail in FIG. 5. Placement of the pedestal tube 66 within the mandrel 60 is seen in phantom. The base of the mandrel 60 houses several movement mechanisms as will be described below, one of which incorporates an actuator 82 arranged to rotate and translate within a slot 84 in the housing 70.

FIGS. 4-6 further illustrate aspects of the mandrel 60 and incorporated fabric clamping mechanisms. The inner clamping mechanism 76 is shown exploded in FIG. 5 and comprises a first disc 90 and a second disc 92, both supported on the shaft 94. The first disc 90 includes a cavity for receiving and firmly coupling to the top end of the shaft 94, while the second disc 92 includes a through bore 96 sized larger than the shaft. A coil spring 98 concentric around the shaft 94 is constrained between an enlarged circular cup 100 and a second disc 92. The distance between the fixed first disc 90 and cup 100 places the spring 98 in compression and presses the first and second discs 90, 92 together. A plurality (preferably three) of small arcuate ribs 102 project from the second disc 92 toward the first disc 90. Although not shown, the first disc 90 may include similarly-configured cavities for receiving the ribs 102. The inner clamping mechanism 76 further includes a plurality of thin fingers 104 spaced around the shaft 94 that extend into cavities formed within and cooperate with the second disc 92. As will be explained below, the entire assembly of the inner clamping mechanism 76 may be axially displaced with respect to the mandrel housing 70.

Although a complete description of the steps in a fabric covering procedure will be provided below, two early steps are illustrated in FIGS. 4A and 4B. The fabric tube 62 is held by the inner clamping mechanism 76 by separating the first and second discs 90, 92 and placing one end of the tube therebetween. The fabric is trapped between the arcuate ribs 102 of the second disc 92 and the opposed surface or cavities of the first disc 90. The result is seen in FIG. 4A. Subsequently, the pedestal tube 66 is passed down over the inner clamping mechanism 76 with the fabric tube 62 projecting upward through its hollow interior. The lower end of the pedestal tube 66 rests on a cylindrical base 110 and is held thereon by an interference fit with an upstanding tubular boss 112 (FIG. 4A). The shaft 94 and fingers 104 of the inner clamping mechanism 76 pass through apertures in the boss 112 such that the first clamping mechanism may be axially displaced with respect to the base 110 and pedestal tube 66. The tube 66 defines a step or pedestal 114 on one end sized to receive and support an inflow edge of the heart valve support stent 18 (shown exploded in FIG. 4B).

With reference now to FIGS. 4B and 6, the peripheral spacing of the outer and inner clamping mechanisms 74, 76 with respect to the support stent 18 will be described. As seen in FIG. 4B, the support stent 18 includes three commissures 120 alternating with three cusps 122. As mentioned above, and as seen in FIG. 6, there are preferably three clamp members 78 oriented 120° with respect to one another, and three arcuate ribs 102 also oriented 120° with respect to one another. When properly positioned on the pedestal 114, the support stent 118 will be oriented such that the commissures 120 are located between two adjacent clamp members 78 of the outer clamping mechanism 74, and the cusps 122 register with the clamp members. Similarly, the arcuate ribs 102 provided on the second disc 92 of the inner clamping mechanism 76 are peripherally located in registry with the clamp members 78. That is, the cusps 122 of the support stent 18 align with the three discrete clamping members of both the outer and inner clamping mechanisms 74, 76. The significance of this relative orientation will be explained below in the context of the exemplary process steps.

Figure 6A:
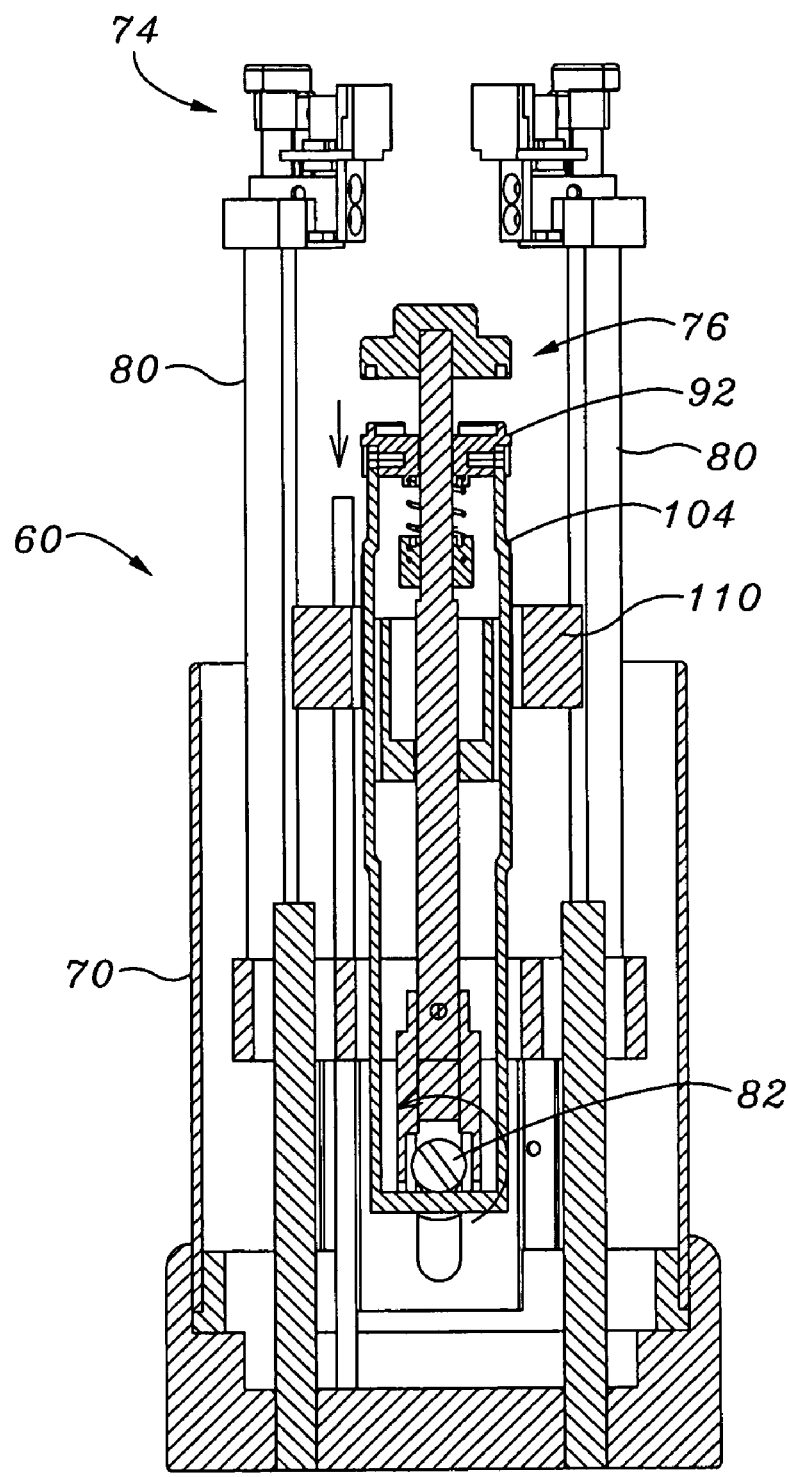
FIGS. 6A and 6B are longitudinal sectional views through the mandrel of FIG. 3 schematically illustrating an internal movement mechanisms.
Figure 6B:
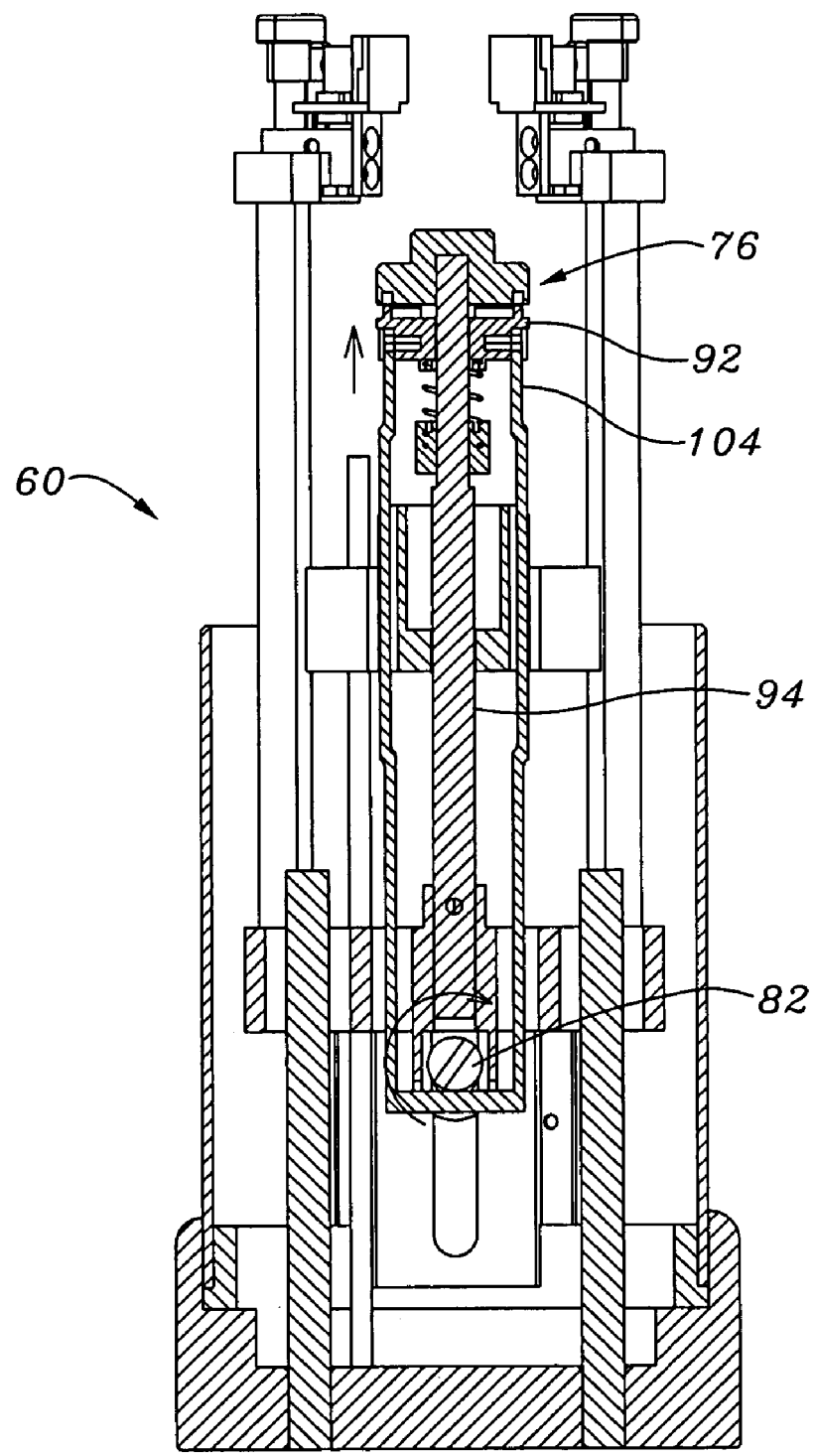

FIGS. 6 and 6A-6B schematically show some of the internal details of the mandrel 60. The actuator 82 is shown rotated in opposite directions in FIGS. 6A and 6B to cause axial displacement of the lower disk 92 of the first clamping mechanism 76. Those of skill in the art will understand that numerous gear trains can be used to translate the rotation of the actuator 82 into axial translation of the lower disk 92 and connected parts, and therefore further description will be omitted herein for the sake of brevity. Also not shown is a mechanism for axially translating the outer and inner clamping mechanisms 74, 76 including the stanchions 80 with respect to the cylindrical base 110 to which the pedestal tube 66 is coupled, as described above with respect to FIG. 4B. It should thus be understood by the reader that the various mechanisms for axially translating the relatively moving parts of the mandrel 60 are not further illustrated or described for the sake of brevity, and because the specifics of none are considered particular to the present invention. It is worth noting, however, that these movement mechanisms may be manually operated, such as with the actuator 82, or servomotors or other such electrical devices may be relied on for logic-controlled, power-assisted or more precise movements.

A number of steps in a fabric covering procedure are shown in FIGS. 7A-7G, with only the pertinent portions of the mandrel 60 illustrated. The process generally involves wrapping the tubular length of fabric 62 over the support stent 18 and then, using the mandrel 60 and associated components, retaining tension in the tubular length of fabric such that it is held tautly along the undulating outflow edge of the support stent. Once the fabric 62 is taught around the support stent, and is maintained in this state without manual assistance, it can be fastened around the support stent by adding the seam 50 as indicated in FIG. 2.

FIG. 7A shows the tubular fabric 62 and pedestal tube 66 exploded from the outer and inner clamp mechanism 74, 76. As mentioned, the first and second discs 90, 92 are biased against one another by the spring 98. By retracting the second disc 92 using the actuator 82, a first end of the fabric tube 62 may be stretched around the first disc 90 and interposed between the two discs. Once a first end of the fabric tube 62 is between the discs 90, 92, they are permitted to come back together which traps the first end of the fabric tube, as seen in FIG. 4A. Specifically, the three arcuate ribs 102 seen in FIG. 5 clamp discrete circumferential segments of the fabric tube 62 against the first disc 90. As mentioned above, the three locations at which the ribs 102 clamp the fabric tube 62 correspond to the cusps of the support stent 18.

Next, the pedestal tube 66 passes over the free end of the fabric tube 62 into engagement with the base 110 and cylindrical boss 112, as seen in FIGS. 4B and 7B. Again, the tube 66 fits closely around the boss 112 in an interference fit, and axial movement of the base 110 causes equivalent axial movement of the boss and tube. It should again be mentioned here that axial movement of the base 110 may occur independently from movement of either the outer clamping mechanism 74 or the inner clamping mechanism 76.

FIGS. 4B and 7C show a step of placement of the support stent 18 around the fabric tube 62 and on the pedestal 114. The pedestal 114 is positioned just inward from the open mouth of the pedestal tube 66 for purposes that will be explained below. In the exemplary embodiment, the support stent 18 has a scalloped or undulating inflow edge and the pedestal 114 is likewise contoured such that the support stent can only be oriented in one of three rotational positions, 120° apart. Because the support stent 18 is tri-symmetric, the contoured shape of the pedestal 114 ensures that the commissures 120 are placed intermediate adjacent clamp members 78, as seen best in FIG. 4B. Alternatively, the pedestal 114 may be planar and the tube 66 provided with markings to indicate to the user the proper orientation.

In FIG. 7D, the stabilizing cone 68 is shown positioned within the fabric tube 62 and support stent 18. The stabilizing cone 68 provides a measure of stability to the support stent 18 as the free end of the fabric tube 62 is inverted, wrapped back over the support stent 18, and captured by the outer clamping mechanism 74. As seen, the individual clamp members 78 hold the fabric tube at three discrete locations corresponding to the valve cusps 122. At this stage, the fabric tube 62 is captured on both ends, first inside the pedestal tube 66 by the inner clamping mechanism 76 and then on the other end by the outer clamping mechanism 74. The fabric tube 62 passes over the outflow edge of the support stent 18 and remains relatively loose.

In FIG. 7E, the stabilizing cone 68 has been removed and both the outer and inner clamping mechanisms 74, 76 are displaced slightly to the left, away from the support stent 18, which is held fixed with respect to the pedestal tube 66. That is, the mandrel 60 include a mechanism for either translating the base 110 and cylindrical boss 112 to the right with respect to the outer and inner clamping mechanisms 74, 76, or visa versa. This movement tightens the fabric tube 62 around the support stent 18. Although the three clamping locations of both the outer and inner mechanisms 74, 76 cause overall movement of both ends of the fabric tube 62, the three discrete points at which the clamping mechanisms hold the fabric tube creates more tension in the portions of the fabric corresponding to the support stent cusps 122. Because the pedestal 114 is located just inward from the open mouth of the tube 66, the outer clamp members 78 pull and stretch the fabric into the arcuate depression at the cusps 122. At the same time, the ribs 102 of the inner clamp mechanism 76 provided a directly opposite tensile force such that the fabric tube 62 eventually conforms closely to the undulating outflow edge of the support stent 18.

Figure 7F:
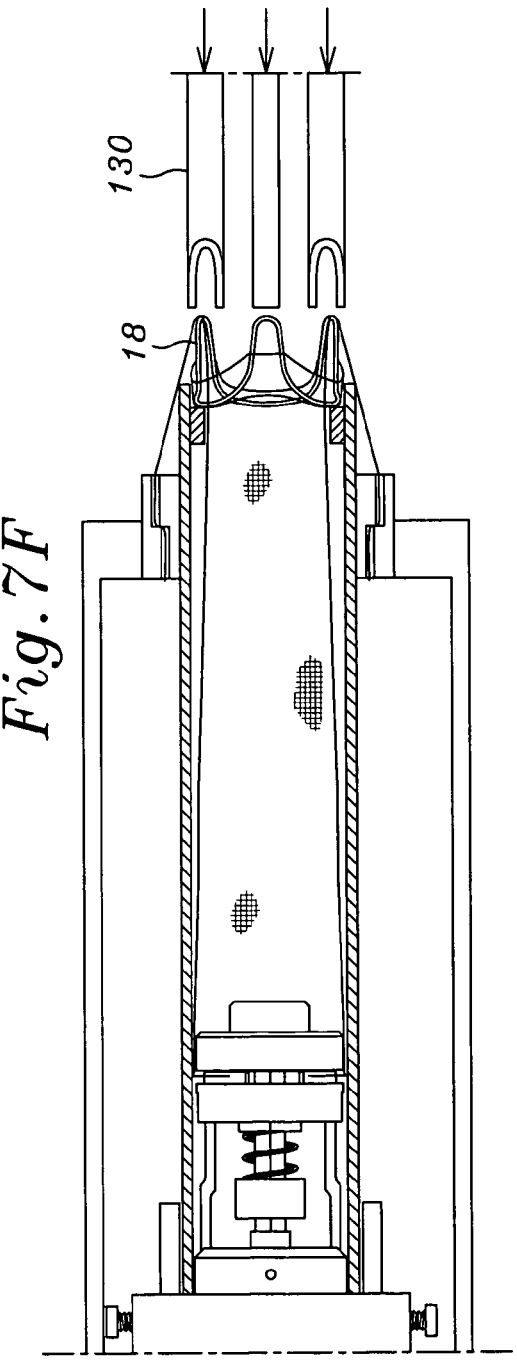
Figure 7G:
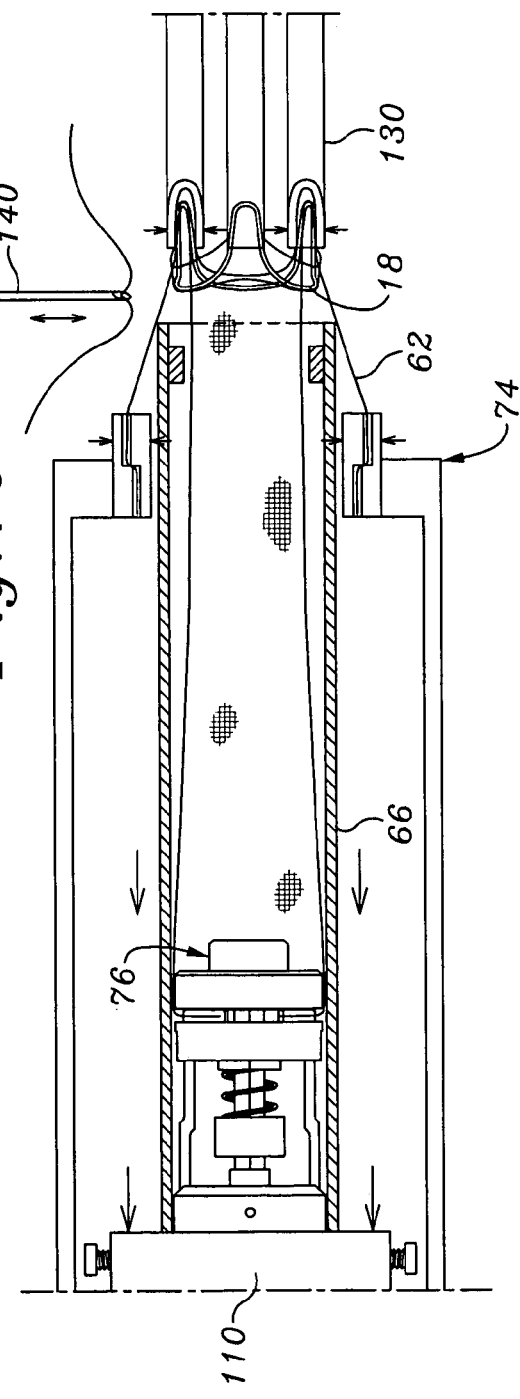

At this stage, multiple commissure clamps 130 seen in FIG. 7F are introduced on the outflow side of the support stent 18. The multiple commissure clamps 130 are arranged to hold the fabric-covered support stent commissures 120, as seen in FIG. 7G. The commissure clamps 130 are schematically shown and may take many forms, including simple spring-biased fingers. As will be explained below, the commissure clamps 130 rotate in concert with the mandrel 60, and thus are preferably mounted for rotation on a spindle (not shown) of a sewing machine 150.

Once the commissures 120 are clamped, the base 110 displaces to the left which causes equivalent displacement of the pedestal tube 66. The outer and inner clamping mechanisms 74, 76 remain stationary so that the only effect is separation between the open mouth of the pedestal tube 66 and the support stent 18. The gap created between the tube 66 and support stent 18 provides space for introduction of a sewing needle 140 to form the seam 50, as in FIG. 2. As mentioned above, the sewing needle 140 may be manually manipulated, or may be part of an electric sewing machine, as will be explained below.

Figure 8:
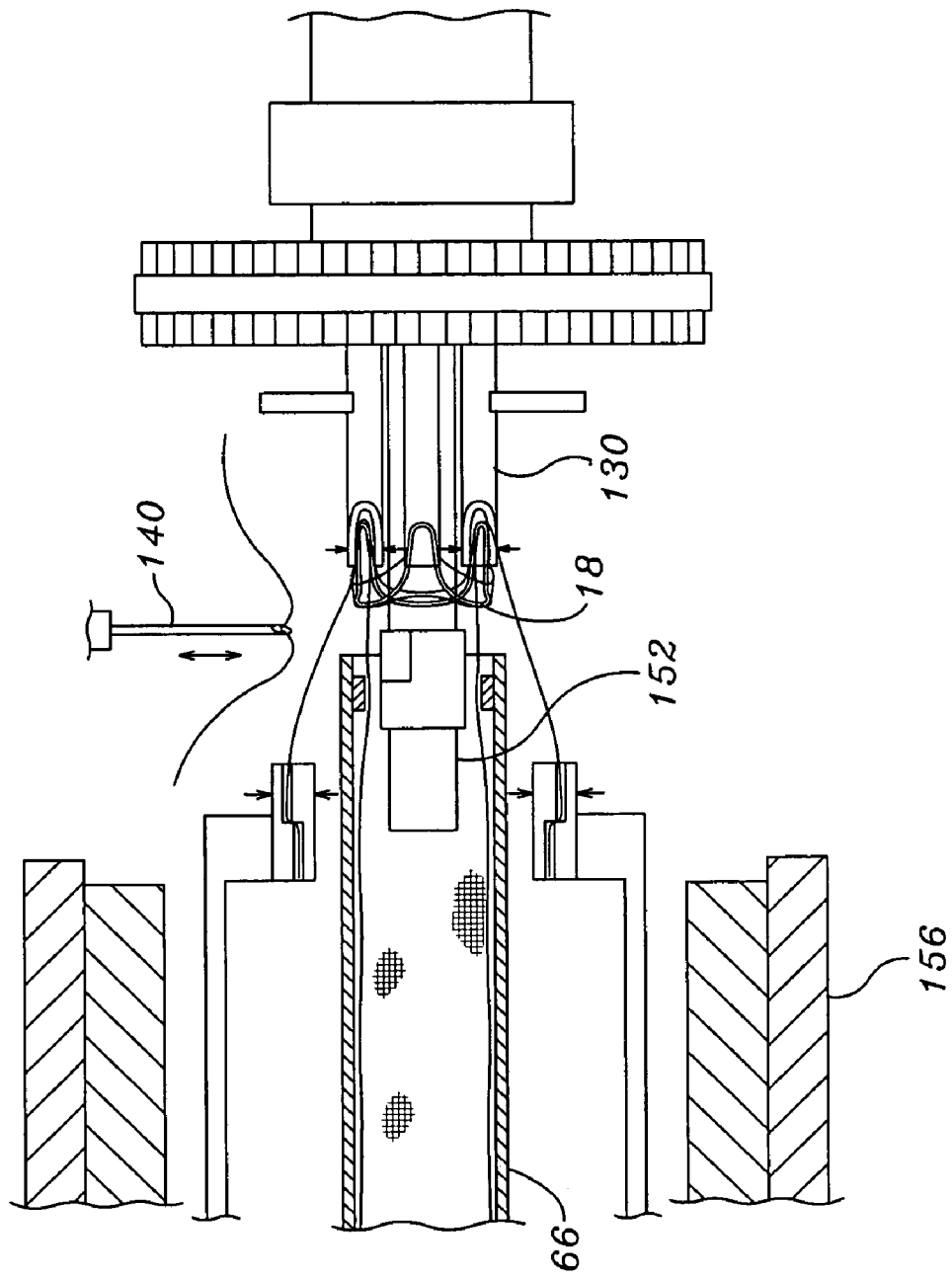
FIG. 8 is a partial sectional view of the mandrel of FIG. 3 in the final stage of the fabric covering procedure seen in FIG. 7G, and shown operating in conjunction with an automated sewing machine system.
Figure 9:
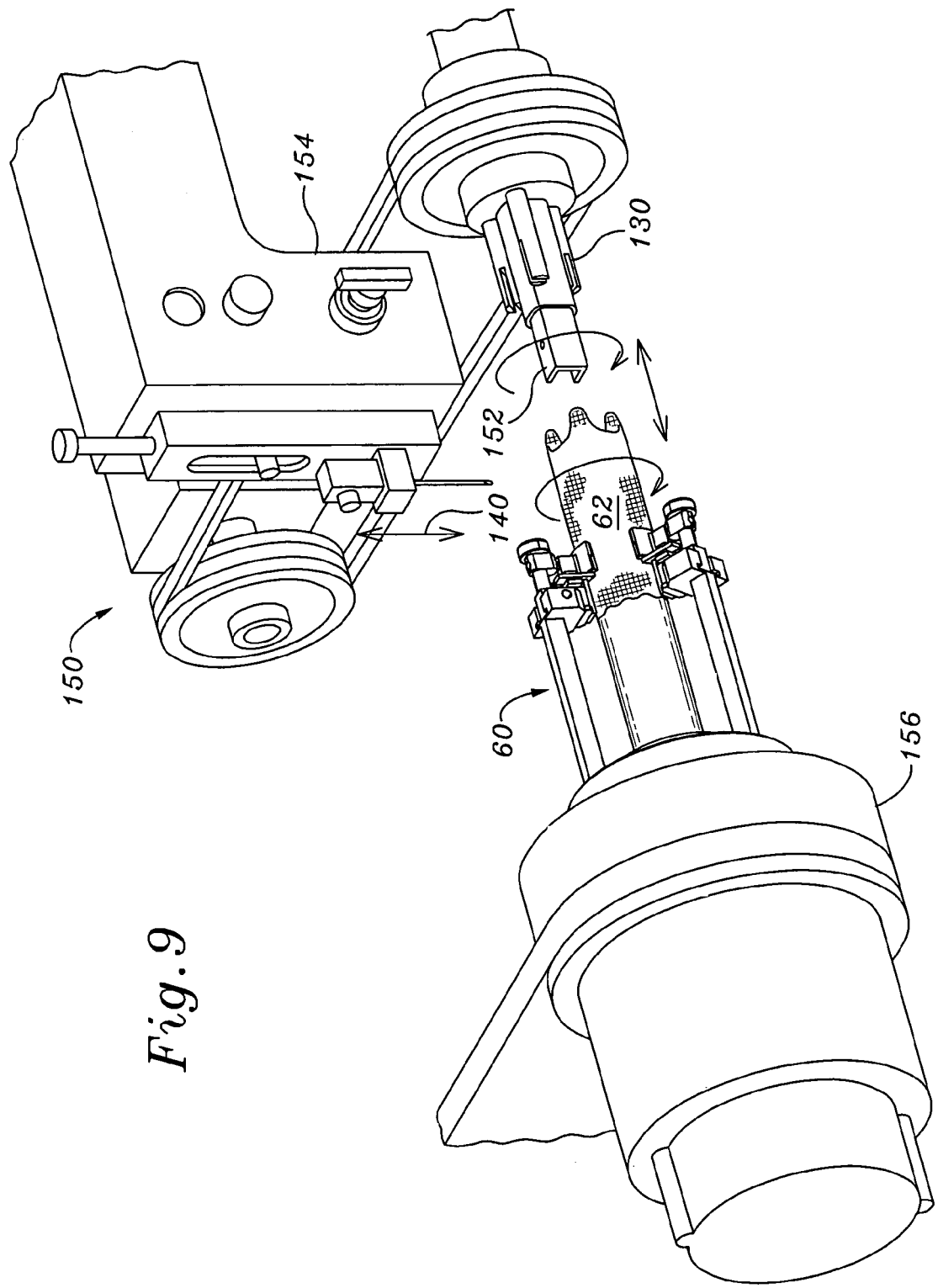
FIG. 9 is a perspective of a portion of an exemplary automated sewing machine system used in conjunction with the mandrel in the fabric covering procedure of the present invention.

FIGS. 8 and 9 show the mandrel 60 coupled with elements of an electric sewing machine 150. FIG. 9 corresponds to the relative positions of the mandrel 60 and commissure clamps 130 seen in FIG. 7F, while FIG. 8 corresponds to FIG. 7G. The sewing machine 150 includes the aforementioned commissure clamps 130 mounted on a spindle (not shown) for rotation around a shuttle channel 152, and a sewing head 154 on which the needle 140 reciprocates. In addition, the sewing machine 150 includes a chuck 156 in which the mandrel 60 is received for rotation about the same axis as the commissure clamps 130. It will be therefore understood that once the pedestal tube 66 retracts, as seen in FIG. 8, the commissure clamps 130 and mandrel 60 within the chuck 156 rotate simultaneously as the sewing needle 140 reciprocates and creates the seam 50 closely adjacent to the inflow edge of the support stent 18. In a preferred embodiment, the stitch 50 is formed a distance of approximately 0.030 inches away from the inflow edge of the support stent 18.

There are a number of different automated stitches that may be performed by the sewing machine 150, including a basic chain stitch and a lock stitch. To ensure integrity of the heart valve, a lock stitch is preferred. While the present invention is believed to be the first implementation of a sewing machine for assembling heart valves, the shuttle bobbin system described below for creating a lock stitch is believed to be novel in more general terms. In particular, the use of a very small reciprocating shuttle with bobbin and corresponding method is believed to be a novel arrangement for creating lock stitch seams which is applicable to finished products other than heart valve components. For instance, tubular stent grafts requiring a fabric covering may be assembled using the system described herein.

FIGS. 10-19 illustrate details of an exemplary system for forming a seam in the fabric tube around the support stent 18. FIGS. 10A and 10B are perspective views of a needle and shuttle bobbin subsystem 160 for use with the exemplary sewing machine 150. A phantom fabric tube 162 draped over a heart valve stent as described above is shown held by the commissure clamps 130, and the other end is held by the mandrel 60 (not shown) to maintain the fabric taut. The subsystem 160 includes the needle 140, the shuttle channel 152, and a shuttle 164 that reciprocates longitudinally within the channel 152. A driver mechanism for the shuttle 164 is not shown in FIGS. 10-15 for clarity, but will be explained with respect to FIGS. 16 and 17. The channel 152 is open on one side as shown and includes aligned through holes 166 (see FIG. 11) in the opposed side walls for passage of the needle 140. The support stent 18 within the fabric tube 162 is not shown, although it will be understood that the needle 114 forms the seam in the fabric tube closely adjacent the inflow end of the tubular stent.

Figure 10A:
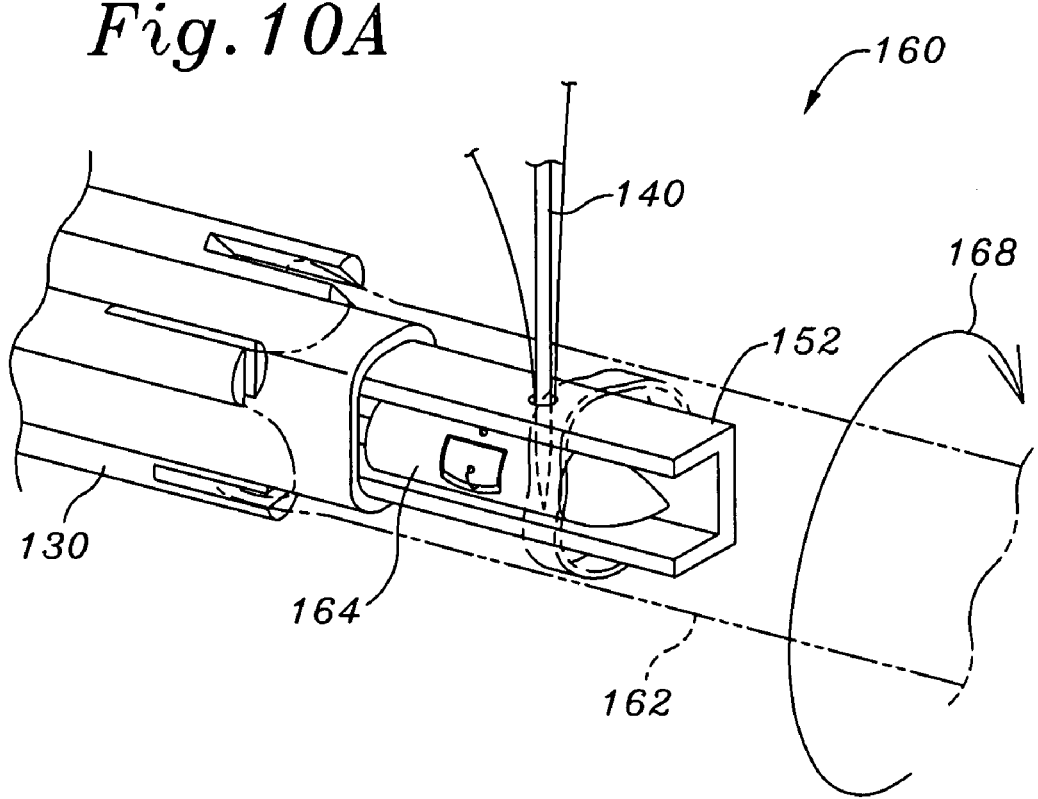
FIGS. 10A and 10B are perspective views of a needle and shuttle bobbin subsystem of the exemplary automated sewing machine system.
Figure 10B:
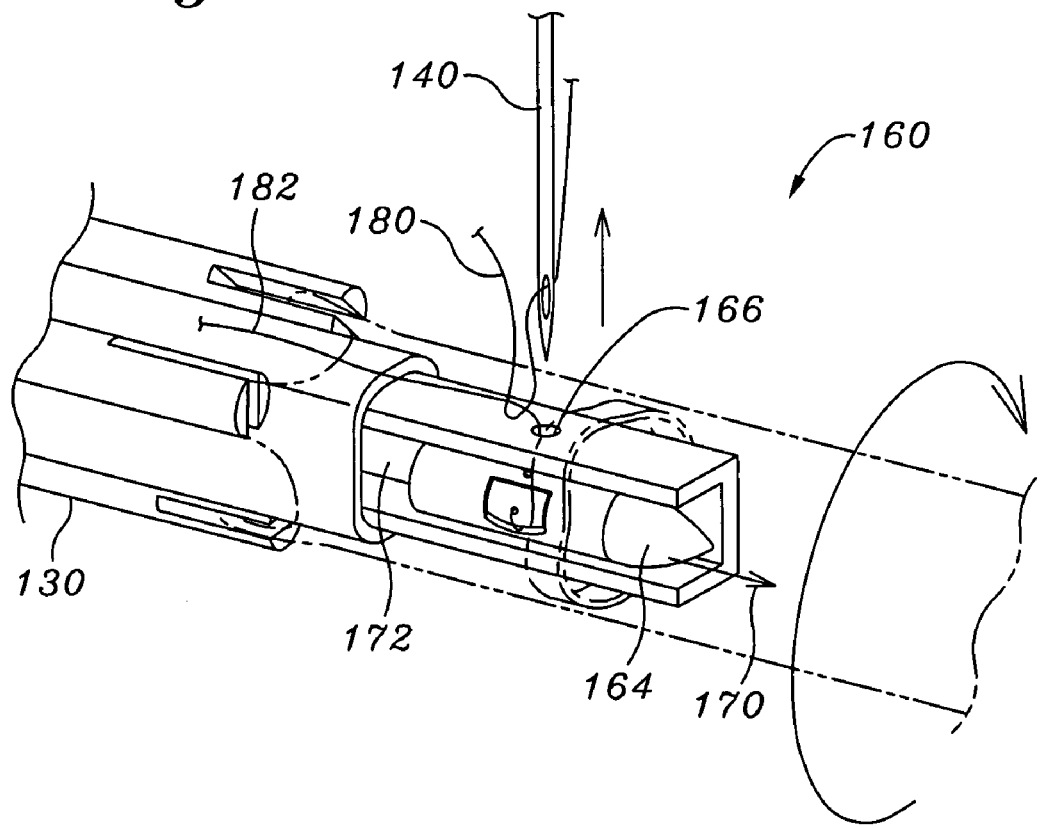

FIGS. 10A and 10B show the overall positioning of the needle 140 with respect to the clamps 130 and fabric tube 162, in relation to the channel 152 and shuttle 164 therein. The rotational arrow 168 indicates movement of the support stent and fabric tube 162 as indexed by rotation of the commissure clamps 130 and mandrel 60 (not shown). As these components rotate, the needle and 40 and shuttle 164 reciprocate to form the generally circular seam. The shuttle 164 floats within and reciprocates linearly with respect to the channel 152, as indicated by the movement arrow 170 in FIG. 10B. In this regard, the shuttle 164 has generally a tapered or bullet-shaped distal tip and is driven by a rod 172 that imparts linear motion thereto (again, the driving mechanism will be described with respect to FIGS. 16 and 17 and a simple rod 172 is only shown for schematic purposes).

FIG. 10B illustrates the end result of one cycle of the needle 140 into and out of the aligned holes 166. Namely, a thread 180 carried by the needle 140 loops around a segment of another thread 182 that is carried by the shuttle 164. As seen best in FIG. 16, looping the needle thread 180 around the bobbin thread 182 captures that loop on the inside of the fabric tube 162. Repetitive cycles of this looping operation at different locations around the fabric tube 162 creates the lock-stitch seam. For further explanation of a lock-stitch seam, albeit with a rotary bobbin, the reader should refer to the web site http://home.howstuffworks.com/sewing-machine2.htm.

Figure 11:
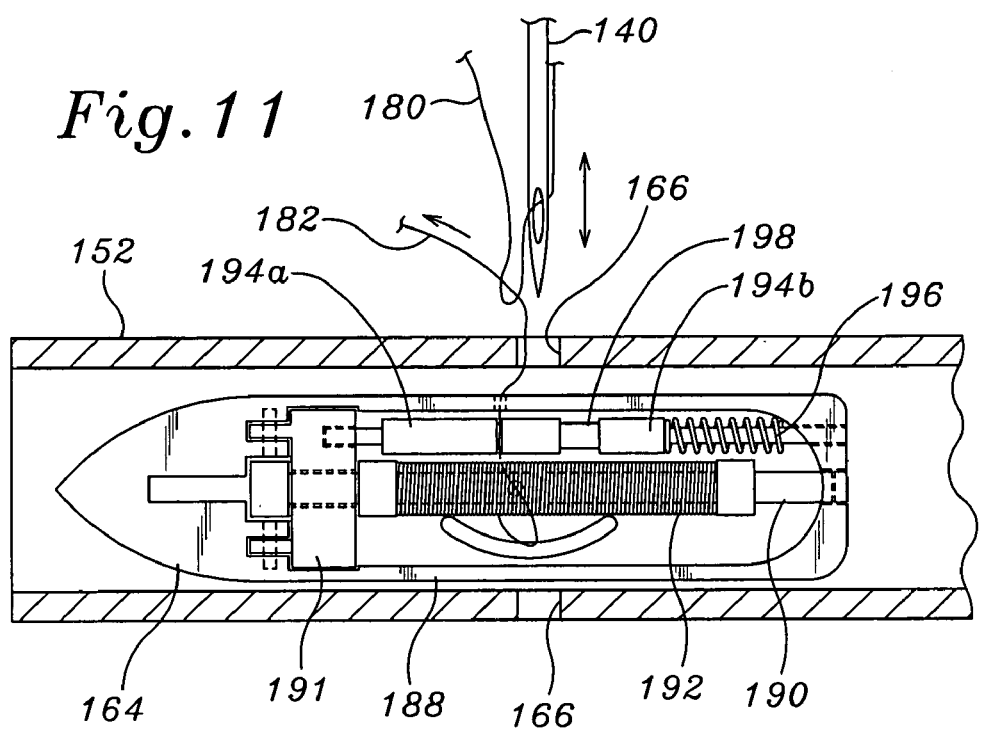
FIG. 11 is an enlarged partial sectional view of the needle and shuttle bobbin subsystem.
Figure 12:
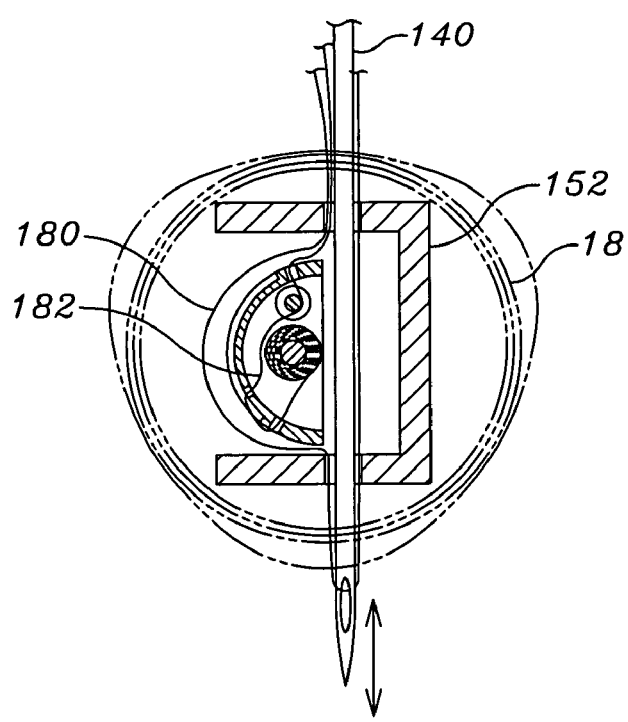
FIG. 12 is a transverse sectional view through the needle and shuttle bobbin subsystem with the needle in the down position.
Figure 13:
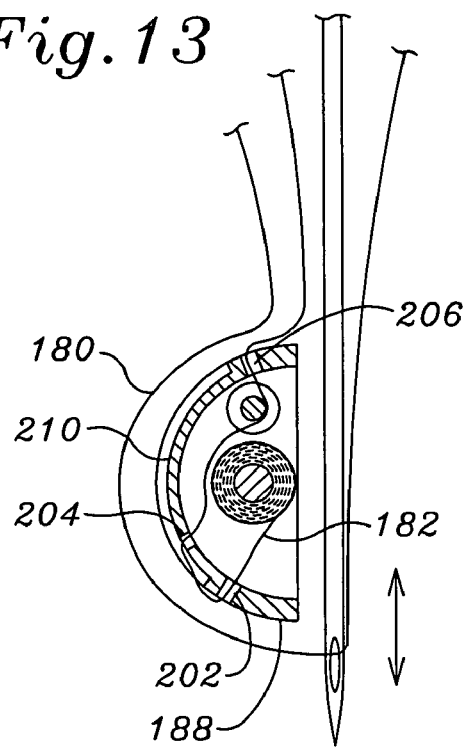
FIG. 13 is an enlarged view similar to FIG. 12 better illustrating an exemplary thread path.

FIGS. 11-13 present a series of sectional and partial sectional views of the needle and shuttle bobbin subsystem, which includes the aforementioned channel 152 and reciprocating shuttle 164. The shuttle 164 comprises a housing 188 formed in an elongated half-tube that is open on one side. The internal components of the shuttle 164 mounted within the housing 188 include a bobbin shaft 190 on which fastens a coil 192 of the bobbin thread 182. The bobbin shaft 190 rotates within cooperating bores and a small pivoting door 191 retains it in place and permits easy replacement when the thread 182 is used up. The free end of the bobbin thread 182 passes through a gap between a pair of tensioning members 194a, 194b that are biased toward each other by a small spring 196. The spring-biasing of the two members 194a, 194b toward one another creates a frictional drag on the bobbin thread 182 so that it does not pay out freely, but instead remains slightly taut when pulled from the coil 192 by the looped needle thread 180. As seen best in FIG. 11, a first tensioning member 194a comprises an enlarged portion of a shaft, while the second tensioning member 194b slides on the shaft and includes a neck region 198 that permits the user to pull it back with a finger against the force of the spring 196 when passing the bobbin thread 182 within the gap. Alternatively, both the first and second tensioning members 194a, 194b are machined cylinders (e.g., Delrin) having through bores for mounting on the shaft.

The path of the bobbin thread 182 from the coil 192 out of the housing 188 of the shuttle 164 is seen in FIGS. 12 and 13. The housing 188 is open on one side for easy replacement of the shaft 190 carrying a coil 192 of thread. The bobbin thread 182 passes from the interior to the exterior of the housing 188 through a smile-shaped aperture 202 (see FIG. 14) and then passes through another aperture 204 to the interior of the housing. The arcuate shape of the aperture 202 permits the thread 182 to easily unspool from along the entire length of the coil 192. From there, the bobbin thread 182 passes into the gap between the tensioning members 194a, 194b, and finally out through a third aperture 206 in the housing 188. With reference again to FIG. 10B, the bobbin thread 182 is shown extending up through one of the aligned holes 166 in the channel 152 and then in a direction past the commissure clamps 130. The operator typically captures or otherwise fixes this free end of the bobbin thread 182 at least at the beginning of the sewing operation to provide a starting tension.

The present invention is particularly well-suited for assembling components of a heart valve, which must be done under extremely sanitary conditions in a clean room, for obvious reasons. Certain means for tensioning the bobbin thread in the prior art were unsuited for such an application. For example, one prior tensioning system utilized a felt bumper that was spring-biased against the bobbin thread, and tended to collect dust and shed particles over time. The present invention solves this issue by utilizing the tensioning members 194a, 194b that are solid and designed not to wear and create particles. For example, the tensioning members 194a, 194b may be made of Delrin (acetal), Teflon (polytetrafluoroethylene), or a suitable metal. In addition, it should be understood that the particular arrangement illustrated for applying tension to the bobbin thread 182 is exemplary only, and may be replaced with an alternative, such as a leaf spring arranged to bias the bobbin thread against the inner wall of the shuttle housing 188 or other fixed structure. The shaft-mounted tensioning members 194a, 194b, however, are desirable because of their low cost, low radial profile, and reliability.

Figure 14:
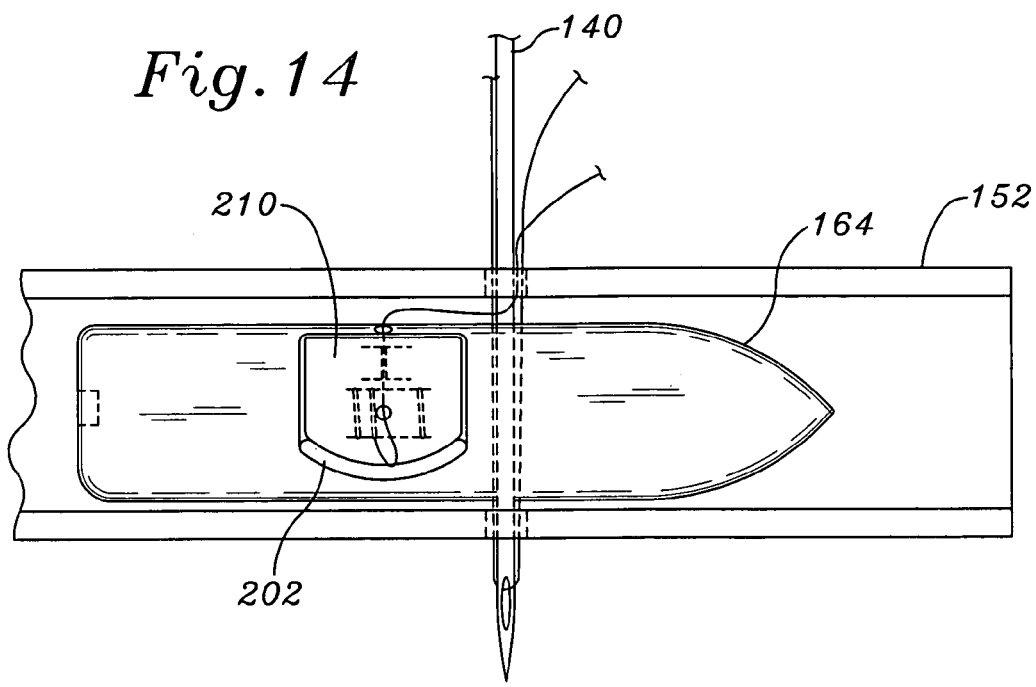
FIGS. 14 and 15 are longitudinal elevational views of the needle and shuttle bobbin subsystem with the needle in down and up positions, respectively.
Figure 15:
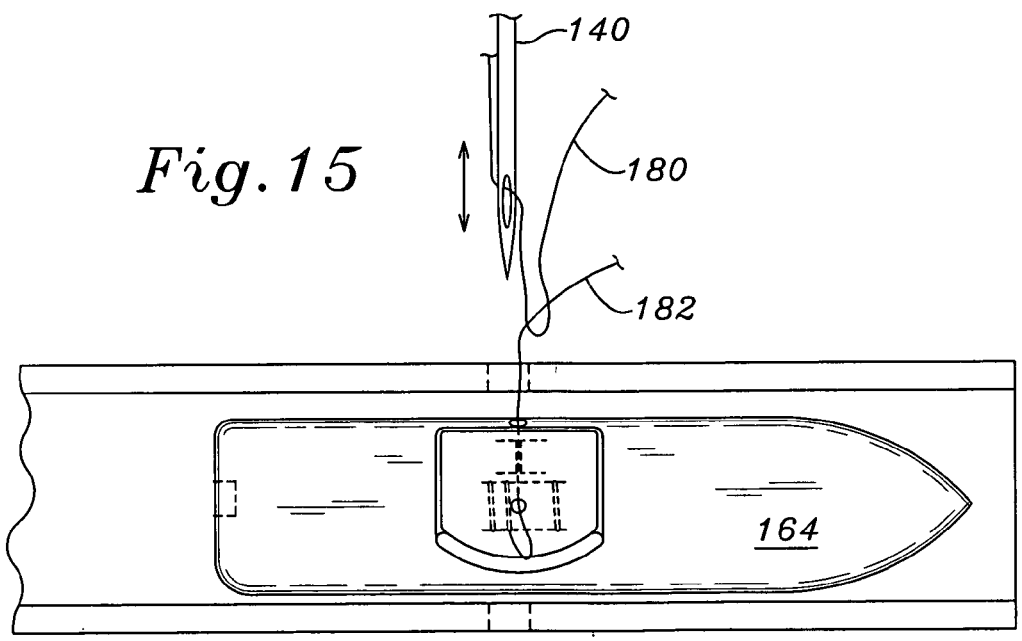

Another feature of the shuttle 164 is a shallow recessed region 210 formed in the exterior surface of the housing 188, as seen in FIGS. 13-15. The recessed region 210 ensures that the bobbin thread 182 is not snagged by the loop of the needle thread 180 as the shuttle 164 reciprocates back-and-forth. That is, the bobbin thread 182 passes to the outside of the housing 188 from aperture 202 to aperture 204. Without the recessed region 210, the looped thread 182 might catch on the looped needle thread 180, for example, as the shuttle 164 passes therethrough.

Figure 16:
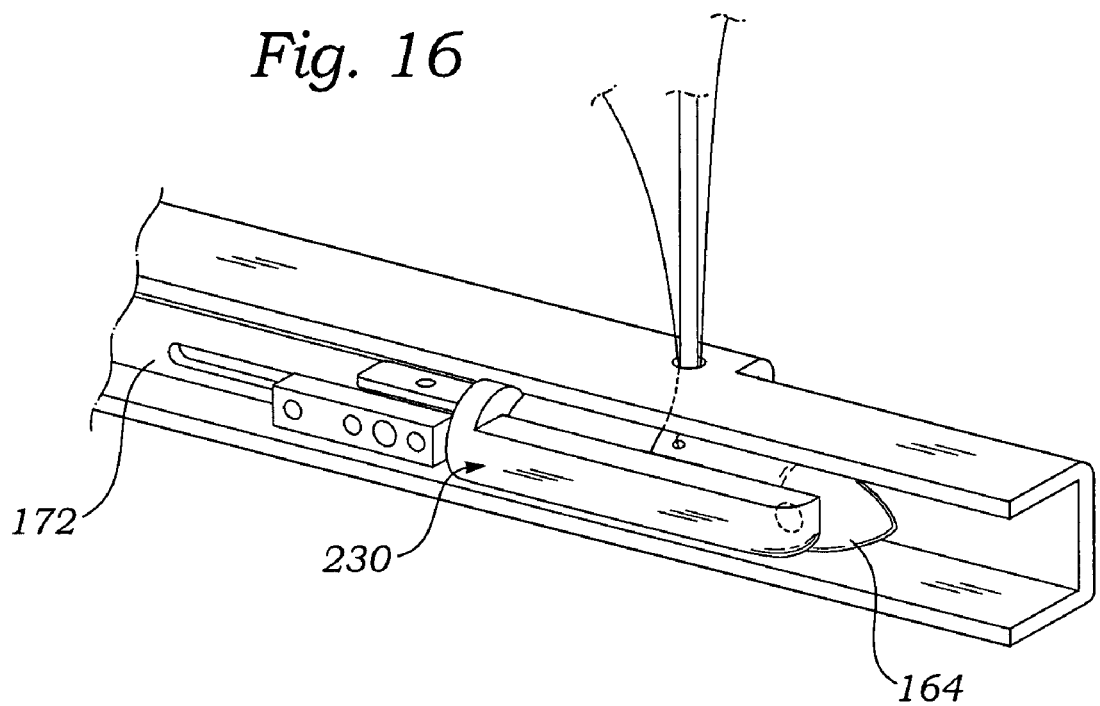
FIGS. 16 and 17 are perspective views of the needle and shuttle bobbin subsystem showing a mechanism for driving the shuttle so that a needle thread may be looped around it.
Figure 17:
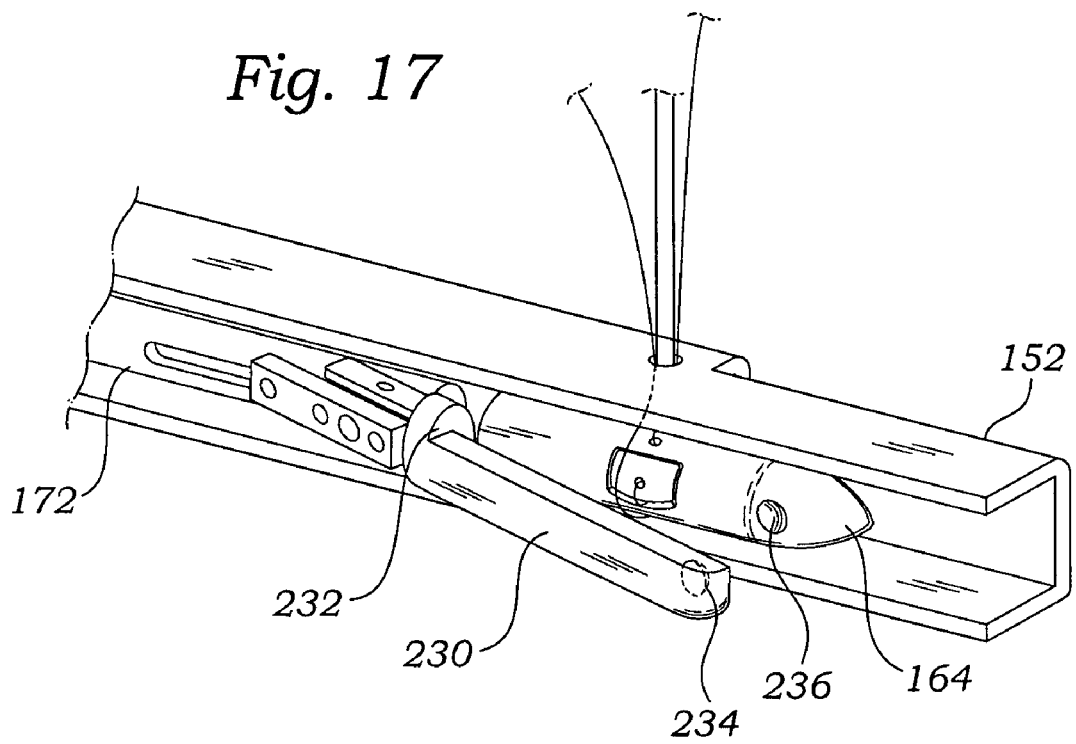

FIGS. 16 and 17 are perspective views of the needle and shuttle bobbin subsystem showing an exemplary mechanism for driving the bobbin so that a needle thread may be looped around it. In particular, the aforementioned rod 172 terminates at its distal end in a coupling for pivoting connection of a driving finger 230. The finger 230 is shown pivoted outward from the rod 172 in FIG. 17 to illustrate the separated nature of the shuttle 164 and its driver. The finger includes a proximal shoulder 232 that contacts the proximal end of the shuttle 164 and pushes it to the right along the channel 152. The finger 230 also includes a spherical bump 234 on its distal end that is received within a spherical depression 236 formed in the distal end of the housing 188 of the shuttle 164. When the finger 230 is pivoted inward against the shuttle 164, as seen in FIG. 16, the bump 234 cooperates with the depression 236 such that proximal movement of the finger 230 pulls the shuttle 164 in a proximal direction along the channel 152.

Figure 18:
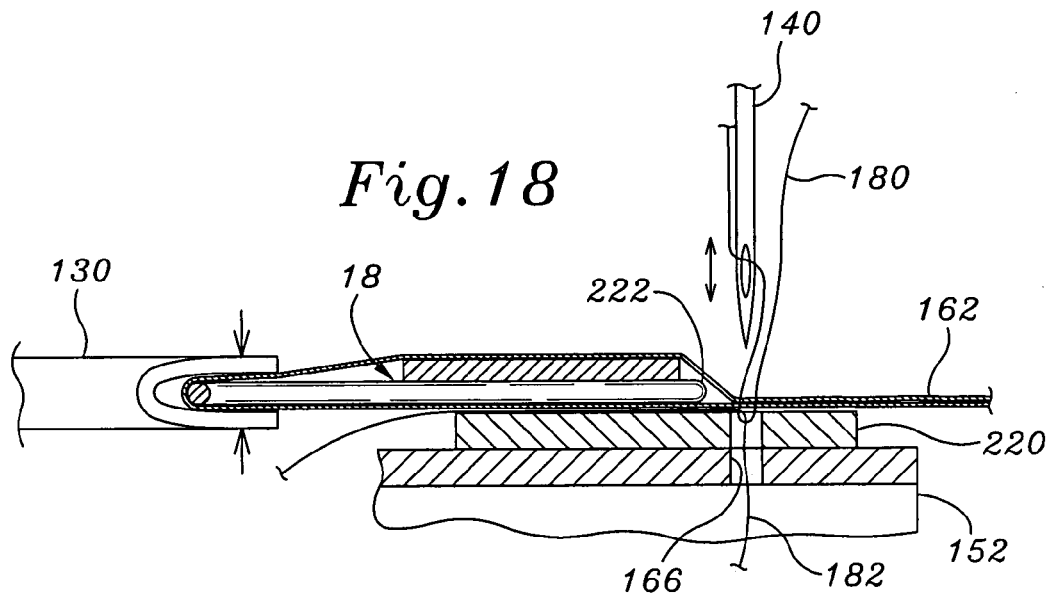
FIG. 18 is a sectional view through one side of the needle and shuttle bobbin subsystem showing the relative position of a fabric-covered heart valve stent.

The operational sequence of the shuttle bobbin subsystem begins with the needle 140 poised above the channel 152 and the shuttle 164 retracted. The needle 140 then descends into the aligned apertures 166 in the channel 152. As the needle 140 begins to rise up or retract from the apertures 166, the loop in the needle thread 180 seen in FIG. 12 is formed. The loop in the needle thread 180 is sized and positioned so as to be aligned with the distal point of the shuttle 164. A built-in dwell in the movement of the needle 140 maintains the loop stationary for a short period of time while the shuttle 164 advances by being pushed by the finger 230. The shuttle 164 advances through the loop of the needle thread 180, and at the same time pulls the bobbin thread 182 along with it. The shuttle 164 essentially floats within the channel 152 so that the loop of the needle thread 180 can pass all the way around between it and the finger 230 to the rear shoulder 232. The loose nature of the connection between the shuttle 164 and finger 230, the shallow nature of the bump 234 and depression 236, and the provision of the recess 210 in the housing 188 of the shuttle 164, all combine to facilitate passage of the needle thread 180 around the shuttle. The needle 140 continues to retract out of the apertures 166 thus pulling the loop of the needle thread 180 with it, and capturing a segment of the bobbin thread 182. At this stage, the rod 172 retracts in a proximal direction which, via the finger 230, pulls the shuttle 164 backwards in preparation for another cycle FIG. 18 is a sectional view through one side of the needle and shuttle bobbin subsystem 160 showing the relative position of a fabric-covered heart valve stent, and illustrates one loop in the lock-stitch seam described. The needle 140 is retracted out of the apertures 166 (a secondary ring 220 having similar aligned apertures may also be provided for guiding the needle 140) and its thread 180 is looped around the bobbin thread 182 on the inside of the fabric tube 162. The seam thus formed is close to the inflow edge 222 of the heart valve support stent 18. Again, during this operation the commissure clamps 130 remain closed on the commissures, while the opposite end of the fabric tube 162 is clamped by the mandrel 60 (not shown off the right of the page).

The aforementioned shuttle bobbin assembly is believed novel because of the small size of the shuttle 164. More particular, the fabric tube 162 generally corresponds to the diameter of the heart valve support stent 18, both of which are relatively small, about 36 mm or less in diameter. The stationary channel 152 fits within the support stent 18, and thus the shuttle 164 must be even smaller still. The diametric dimension (analogous to the diameter, or the largest diametric dimension thereof) of the shuttle 164 is about 8 millimeters or less.

As previously mentioned, the inflow edge of the support stent 18 may be serpentine, scalloped, or undulating. To accommodate this contour, the location of the inflow edge of the support stent 18 translates axially as it rotates with respect to the axially stationary sewing needle 140, or vice versa. In a preferred embodiment, both the commissure clamps 130 and mandrel 60 within the chuck 156 translate axially as they rotate and the sewing needle 140 creates the seam 50. One way to do this is through a predetermined axial movement pattern implemented by cams or other such mechanisms and based on a predicted shape of the inflow edge of the support stent 18.

However, the support stent 18 may not be manufactured to precise tolerances, and because it is desirable to form the seam 50 as close as possible to the inflow edge a more accurate registration system may be necessary. For example, prior to forming the seam 50, the support stent 18 within the fabric tube 62 may be rotated a full turn while an ultraviolet light shines on the inflow edge thereof. Certain materials used in making the support stent 18 fluoresce when illuminated with ultraviolet light so that a special camera can map and record the precise contours of its inflow edge. For example, the support stent 18 often includes a MYLAR (polyethylene terephthalate) band which efficiently fluoresce upon exposure to ultraviolet light. Once the contour of the inflow edge of the particular support stent 18 is known, the sewing operation can commence that contour fed to a computer that controls axial movement of the spindle-mounted commissure clamps 130 and mandrel 60.

Figure 19:
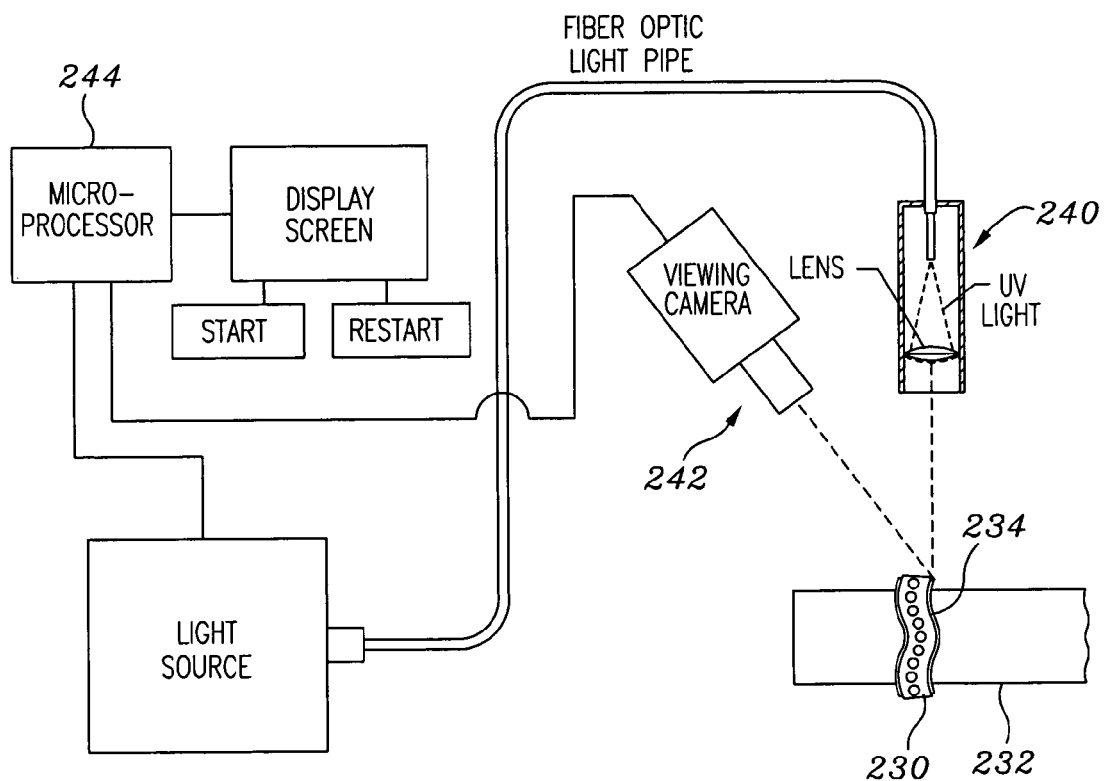
FIG. 19 is a schematic view of a system for mapping an uneven edge of a heart valve stent for proper seam positioning.

FIG. 19 is a schematic view of a system for mapping an uneven edge of an annular heart valve stent 230 for proper seam positioning. The stent 230 is shown mounted over a generic tube 232, although this schematically represents the same configuration as seen in FIG. 16, with the support stent 18 mounted around the shuttle channel 152. One edge 234 is shown having an undulating or serpentine configuration which is the case with some heart valve stents. In order to form a seam in a fabric tube close to this edge, the uneven shape must be accommodated by moving either the stent 230 or the needle 140. As described above, the assembly of the commissure clamps 130 and mandrel 60 move axially in concert to account for the uneven edge of the support stent 18. Although the nominal curvature of the edge 234 may be known, and thus programmed into a movement mechanism of the sewing machine, certain manufacturing tolerances may interfere with forming a seam to close to the inflow edge. In order to form the seam closer to the edge 234, the system in FIG. 19 is utilized to first map the edge, which information is then programmed into the sewing machine movement mechanism.

More particularly, an imaging system including an illumination component 240 and a recording component 242 maps the edge 234. In one exemplary embodiment, the illumination component 240 comprises an ultraviolet light that shines on the edge 234 and causes a portion of the stent 230 to fluoresce. Often, heart valve stents are made with polymers such as Mylar that can be designed to fluoresce under ultraviolet light. Although a fabric tube surrounds the stent 230, the edge 234 can be seen because of its fluorescence. The viewing camera 242 records the contours of the edge 234 as it is rotated, and the information is fed into a microprocessor 244, which ultimately controls the movement of the sewing machine components. In this manner, the precise contour of each individual stent 230 can be measured just prior to the fabric tube being sewn therearound. This ensures that seam can be formed very close to the edge 234, preferably within about 0.030 inches (0.762 mm). Because of the proximity of the seam to the edge 234, and the tension that is continually applied to the fabric tube, the fabric pulls the seam close against the inflow edge when the sewing operation is done.

The above description provides the essential elements of forming the seam 50 in the fabric tube 62. It should be noted that a number of commercial sewing machines 150 may be utilized to mechanize the final step of forming the seam 50, although certain modifications must be made such as the addition of the mandrel-holding chuck 156. The portion of the system comprising the axially moving shuttle 164 and sewing head 154 may be part of a zig-zag shuttle sewing machine which makes use of an archway shuttle. Conventional shuttle machines incorporate a dwell in the reciprocal motion of the sewing needle 140, and the particular machine used in the present system desirably includes a stop motion dwell for the needle 140. Such sewing machines can be obtained from Sew Fine, LLC of San Francisco, Calif. (www.Alsew.com).

It will also be appreciated by those of skill in the relevant art that various changes may be made to the examples and embodiments of the invention described in this provisional application, without departing from the intended scope of the invention. The particular embodiments of the invention described herein are thus to be understood as examples of the broader inventive concept disclosed in this application.

What is claimed is:

1. A system for assembling components of a flexible leaflet prosthetic heart valve having a generally tubular fabric-covered support stent defining a central axis, the system comprising:

a mandrel for retaining tension without manual assistance in a tubular length of fabric wrapped over an outflow end of a heart valve support stent, wherein the outflow end includes an undulating contour and the mandrel is adapted to retain tension in the tubular length of fabric so that it conforms to the undulating contour;

a pedestal tube that fits on the mandrel and holds the support stent, the pedestal tube having a pedestal adjacent one end that is contoured to orient the support stent in a particular rotational position; and a means for forming a seam in the tubular length of fabric adjacent the inflow end of the support stent to enclose the support stent.

2. The system of claim 1, wherein the undulating contour of the outflow end includes multiple cusps curved toward an axial inflow end alternating with multiple commissures projecting toward an axial outflow end, and the mandrel includes separate clamps for the fabric corresponding to the stent cusps.

3. The system of claim 2, wherein there are three inflow cusps and three outflow commissures alternating around a periphery of the support stent, and wherein the mandrel clamps the fabric beyond an axial inflow end of the stent in peripheral locations corresponding to the cusps.

4. The system of claim 3, wherein the mandrel includes an outer clamping mechanism comprising three clamp members oriented 120° apart in each of which is adapted to clamp a section of fabric.

5. The system of claim 4, wherein the mandrel includes an inner clamping mechanism comprising two disks between which one end of the tubular length of fabric may be clamped.

6. The system of claim 5, wherein the pedestal tube, outer clamping mechanism, and inner clamping mechanism are all relatively axially movable.

7. The system of claim 1, wherein the means for forming a seam comprises an electric sewing machine.

8. A system for assembling a prosthetic heart valve, comprising:

two components of a prosthetic heart valve, one of which is a generally tubular prosthetic heart valve support stent having an outflow end with an undulating contour, and the other of which is a tubular length of fabric; and a mandrel having at least one clamp for holding and maintaining the tubular length of fabric wrapped around the outflow end in a taut fashion such that the tubular length of fabric conforms to the undulating contour.

9. The system of claim 8, wherein:

the undulating contour of the support stent includes multiple cusps curved toward an axial inflow end alternating with multiple commissures projecting toward an axial outflow end;

the mandrel is disposed beyond the inflow end of the support stent;
the system further including:
multiple commissure clamps arranged to hold the fabric-covered support stent commissures.

10. The system of claim 9, further including:
an electric sewing machine having a needle, the electric sewing machine including a shaft for rotating the commissure clamps, wherein the needle is positioned to form a seam in the fabric covering at the inflow end of the support stent, and wherein the sewing machine includes a chuck for receiving and rotating the mandrel about the stent axis in conjunction with the commissure clamps.

11. The system of claim 10, wherein the sewing machine is adapted to axially displace the commissure clamps as it rotates, and the chuck is adapted to axially displace the mandrel in conjunction with the commissure clamps.

12. A method of assembling a prosthetic heart valve, comprising:
providing a generally tubular support stent that includes multiple cusps curved toward an axial inflow end alternating with multiple commissures projecting toward an axial outflow end, the support stent having an undulating outflow edge;
wrapping a tubular length of fabric over the support stent;
retaining tension in the tubular length of fabric using mechanization such that the fabric is held tautly along the undulating outflow edge; and
forming a seam in the tubular length of fabric adjacent the inflow edge of the support stent.

13. The method of claim 12, further including:
providing a mechanized support stent holding mandrel;
retaining tension using the mandrel in the tubular length of fabric such that the fabric is held tautly along the undulating outflow edge.

14. The method of claim 13, wherein the mandrel further includes an inner clamping mechanism, an outer clamping mechanism, and a pedestal tube, and wherein the method further includes:
positioning the support stent on the pedestal tube;
securing opposite ends of the tubular length of fabric with the inner and outer clamping mechanisms, respectively; and
tensioning the tubular length of fabric around the support stent by relative movement of both the inner and outer clamping mechanisms with respect to the pedestal tube.

15. The method of claim 14, further including tightening the tubular length of fabric around the support stent by relatively axially displacing the inner and outer clamping mechanisms with respect to the pedestal tube.

16. The method of claim 15, wherein the inner and outer clamping mechanisms each include discrete clamps spaced apart 120° from each other that directly tension the fabric only at the cusps of the support stent.

17. The method of claim 15, further including holding the fabric-wrapped commissures of the support stent with a plurality of commissure clamps and separating the pedestal tube from the support stent by relatively axially displacing the pedestal tube with respect to the commissure clamps.

18. The method of claim 17, wherein the support stent has an undulating inflow edge, the method further including simultaneously axially displacing and rotating the commissure clamps and the mandrel while forming the seam with a needle of a sewing machine system passing through the length of tubular fabric adjacent the inflow edge.

19. A method of assembling a prosthetic heart valve, comprising:
providing a generally tubular heart valve support stent that includes a first edge and an axially-opposite second edge;
wrapping a tubular length of fabric over the first edge of the support stent such that two free ends of the tubular length of fabric continue past the second edge;
retaining tension in the tubular length of fabric such that the fabric is held tautly along the first edge;
mapping the peripheral contour of the second edge of the support stent with an imaging system; and
forming a seam in the tubular length of fabric closely adjacent the second edge of the support stent using an automated sewing system having a needle whose position relative to the second edge is responsive to the mapped contour of the second edge.

20. The method of claim 19, wherein the second edge of the support stent is an inflow edge that has an undulating contour, the method further including simultaneously axially displacing the support stent while forming the seam with the needle of the automated sewing system.

21. The method of claim 20, wherein the first edge of the support stent is an outflow edge that includes multiple cusps curved toward an axial inflow end alternating with multiple commissures projecting toward an axial outflow end, and wherein the step of retaining tension comprises retaining tension without manual assistance so that the tubular length of fabric conforms to the cusps and commissures of the outflow edge.

22. The method of claim 19, wherein the step of forming the seam comprises positioning the needle of the automated sewing system within about 0.030 inches (0.762 mm) of the second edge during the step of forming the seam.

23. The method of claim 19, wherein the imaging system comprises:
an ultraviolet light and a camera.

24. A system for assembling components of a flexible leaflet prosthetic heart valve having a generally tubular fabric-covered support stent defining a central axis, the system comprising:
a mandrel for retaining tension without manual assistance in a tubular length of fabric wrapped over an outflow end of a heart valve support stent, wherein the outflow end includes an undulating contour and the mandrel is adapted to retain tension in the tubular length of fabric so that it conforms to the undulating contour,
wherein the undulating contour of the outflow end includes multiple cusps curved toward an axial inflow end alternating with multiple commissures projecting toward an axial outflow end, and the mandrel includes separate clamps for the fabric corresponding to the stent cusps,
wherein there are three inflow cusps and three outflow commissures alternating around a periphery of the support stent, and wherein the mandrel clamps the fabric beyond an axial inflow end of the stent in peripheral locations corresponding to the cusps,
wherein the mandrel includes an outer clamping mechanism comprising three clamp members oriented 120° apart in each of which is adapted to clamp a section of fabric,
wherein the mandrel includes an inner clamping mechanism comprising two disks between which one end of the tubular length of fabric may be clamped; and
a means for forming a seam in the tubular length of fabric adjacent the inflow end of the support stent to enclose the support stent.

* * * * *